(12) United States Patent
Morimoto et al.

(10) Patent No.: US 8,765,771 B2
(45) Date of Patent: Jul. 1, 2014

(54) CONDENSED PYRIDINE OR CONDENSED PYRIMIDINE DERIVATIVE, AND MEDICINAL AGENT COMPRISING SAME

(75) Inventors: Toshiharu Morimoto, Tokorozawa (JP); Tomoaki Koshizawa, Kawaguchi (JP); Gen Watanabe, Meguro-ku (JP); Tadaaki Ohgiya, Tokorozawa (JP); Nao Yamasaki, Nerima-kui (JP); Noriyuki Inoue, Tokorozawa (JP)

(73) Assignee: Kowa Co., Ltd., Nagoya-shi (JP)

( * ) Notice: Subject to any disclaimer, the term of this patent is extended or adjusted under 35 U.S.C. 154(b) by 0 days.

(21) Appl. No.: 13/806,940

(22) PCT Filed: Jun. 24, 2011

(86) PCT No.: PCT/JP2011/064515
§ 371 (c)(1),
(2), (4) Date: Dec. 26, 2012

(87) PCT Pub. No.: WO2011/162368
PCT Pub. Date: Dec. 29, 2011

(65) Prior Publication Data
US 2013/0102621 A1 Apr. 25, 2013

(30) Foreign Application Priority Data
Jun. 25, 2010 (JP) .................. 2010-144760

(51) Int. Cl.
*A61K 31/519* (2006.01)
*C07D 491/00* (2006.01)

(52) U.S. Cl.
USPC .................. 514/260.1; 544/278; 544/280

(58) Field of Classification Search
USPC .................. 514/260.1; 544/278, 280
See application file for complete search history.

(56) References Cited

U.S. PATENT DOCUMENTS

| | | | |
|---|---|---|---|
| 7,799,782 B2 * | 9/2010 | Munson et al. ............ 514/234.5 | |
| 2004/0138251 A1 | 7/2004 | Boschelli et al. | |
| 2004/0242883 A1 | 12/2004 | Boschelli et al. | |
| 2006/0069123 A1 | 3/2006 | Xia et al. | |
| 2007/0197537 A1 | 8/2007 | Blake et al. | |
| 2008/0070913 A1 | 3/2008 | Boschelli et al. | |
| 2009/0018055 A1 | 1/2009 | Fevig et al. | |
| 2009/0048285 A1 | 2/2009 | Pelcman et al. | |
| 2009/0149458 A1 | 6/2009 | Chen et al. | |
| 2009/0318477 A1 | 12/2009 | Katamreddy | |
| 2010/0056548 A1 | 3/2010 | Aicher et al. | |
| 2010/0292259 A1 | 11/2010 | Kaneko et al. | |
| 2010/0324049 A1 | 12/2010 | Ando et al. | |
| 2011/0105475 A1 | 5/2011 | Roche et al. | |
| 2011/0118286 A1 | 5/2011 | Neelamkavil et al. | |
| 2011/0166165 A1 | 7/2011 | Neelamkavil et al. | |
| 2011/0166167 A1 | 7/2011 | Neelamkavil et al. | |
| 2012/0077826 A1 | 3/2012 | Fevig et al. | |
| 2012/0122846 A1 * | 5/2012 | Calderwood et al. .... | 514/212.07 |

FOREIGN PATENT DOCUMENTS

| | | |
|---|---|---|
| JP | 2008 514700 | 5/2008 |
| JP | 2009 526761 | 7/2009 |
| JP | 2009 532407 | 9/2009 |
| WO | 2004 065389 | 8/2004 |
| WO | WO 2005/056012 A1 | 6/2005 |
| WO | 2005 113560 | 12/2005 |
| WO | 2006 077401 | 7/2006 |
| WO | 2007 115822 | 10/2007 |
| WO | 2008 008887 | 1/2008 |
| WO | 2008 137436 | 11/2008 |
| WO | 2009 041567 | 4/2009 |
| WO | 2009 051119 | 4/2009 |
| WO | 2009 070524 | 6/2009 |
| WO | 2009 127321 | 10/2009 |
| WO | 2010 009195 | 1/2010 |
| WO | 2010 009207 | 1/2010 |
| WO | 2010 009208 | 1/2010 |

OTHER PUBLICATIONS

International Search Report Issued Aug. 23, 2011 in PCT/JP11/64515 Filed Jun. 24, 2011.

Ahren, B. et al., "Inhibition of Dipeptidyl Peptidase-4 Reduces Glycemia, Sustains Insulin Levels, and Reduces Glucagon Levels in Type 2 Diabetes," The Journal of Clinical Endocrinology & Metabolism, vol. 89 (5), pp. 2078 to 2084, (2004).

Nielsen, L. et al., "Pharmacology of exenatide (synthetic exendin-4): a potential therapeutic for improved glycemic control of type 2 diabetes," Regulatory Peptides 117, pp. 77 to 88, (2004).

(Continued)

*Primary Examiner* — Rei-tsang Shiao
(74) *Attorney, Agent, or Firm* — Oblon, Spivak, McClelland, Maier & Neustadt, L.L.P.

(57) ABSTRACT

The present invention relates to provision of a novel compound that has an activity of promoting insulin secretion from pancreatic β cells and thus is useful as a prophylaxis and/or therapeutic agent for diseases caused by hyperglycemia such as diabetes mellitus, and
the compound represented by the following formula (1):

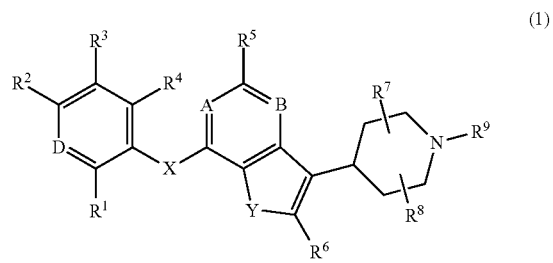

(1)

wherein one of A and B represents a nitrogen atom and the other represents a nitrogen atom or $CR^{10}$, X represents an oxygen atom, a sulfur atom or —$(CH_2)$n-$N(R^{12})$—, Y represents an oxygen atom, a sulfur atom or —$N(R^{13})$—, and $R^1$ to $R^9$ each represent a hydrogen atom or another substituent, or a salt thereof, or a solvate of the compound or the salt.

19 Claims, No Drawings

(56) References Cited

OTHER PUBLICATIONS

Sturgess, N. et al., "The Sulphonylurea Receptor May Be an ATP-Sensitive Potassium Channel," The Lancet, vol. 2, pp. 474 to 475, (Aug. 31, 1985).
UK Prospective Diabetes Study (UKPDS) Group, "Intensive blood-glucose control with sulphonylureas or insulin compared with conventional treatment and risk of complications in patients with type 2 diabetes (UKPDS 33)," The Lancet, vol. 352, pp. 837 to 853, (Sep. 12, 1998).
Extended European Search Report issued Nov. 28, 2013, in Patent Application No. 11798249.6.

\* cited by examiner

CONDENSED PYRIDINE OR CONDENSED PYRIMIDINE DERIVATIVE, AND MEDICINAL AGENT COMPRISING SAME This application is a National Stage of PCT/JP11/064515 filed Jun. 24, 2011 and claims the benefit of JP 2010-144760 filed Jun. 25, 2010.

TECHNICAL FIELD

The present invention relates to a drug that has an action of promoting insulin secretion from pancreatic β cells and thus prevents and/or treats diseases caused by hyperglycemia such as diabetes mellitus.

BACKGROUND ART

The pancreas is an endocrine-exocrine gland tissue derived from the endoderm, and is constituted by endocrine cells, acinar cells and duct cells. The islets of Langerhans, which are endocrine cells, constitute 1% of the entirety of the pancreas, and are mainly classified into four cells. Namely, they are α cells that secrete glucagon, β cells that secrete insulin, δ cells that synthesize and secrete somatostatin, and F cells that synthesize and secrete pancreatic polypeptides. Among these, insulin that is secreted in β cells has an action of decreasing blood glucose as a major physiological function, and is also a sole hormone that shows a hypoglycemic action. Insulin is secreted in pancreatic β cells by sensing the elevation of blood glucose, and is released into the portal veins. The released insulin suppresses glyconeogenesis and glucose output in the liver and promotes glucose uptake in the fat and muscle tissues that are peripheral tissues, thereby acts to retain the blood glucose level of a living body.

Diabetes mellitus is a persistent hyperglycemia state that is caused by lack of insulin, or lack of the action of insulin. Diabetes mellitus is mainly divided into two kinds: insulin dependent diabetes mellitus (IDDM) that is caused by abnormal secretion of pancreatic insulin by an autoimmune disease or the like, and non-insulin dependent diabetes mellitus (NIDDM) that is caused by the decrease of insulin secretion ability due to pancreatic fatigue accompanied with a persistent high insulin state due to lack of the action of insulin (insulin resistance). Persistent hyperglycemia due to diabetes mellitus causes impairment of blood vessels and also causes complications in multiple organs. Typical complications may include diabetic nephropathy, diabetic retinopathy, diabetic neurosis and the like, and decrease in quality of life (QOL), increase in medical expenses, decrease in survival percentage and the like are seen as problems.

For the therapy of diabetes mellitus, an exercise therapy, a dietary therapy and a drug therapy are conducted. Examples of drugs used for drug therapy include drugs for promoting insulin secretion from pancreatic β cells, drugs for improving insulin resistance, drugs for suppressing absorption of sugar, drugs for promoting utilization of sugar, and the like. Among these, insulin secretagogues are expected to improve diabetes mellitus by suppressing hyperglycemia since they can be expected to have an effect of increasing a blood insulin concentration to decrease blood glucose, and sulfonylurea formulations (SU drugs), rapid-acting insulin secretagogues, DPPIV inhibitors (see Non-Patent Document 1), GLP-1 analogues (see Non-Patent Document 2) and the like are actually used in the fields of the therapy of diabetes mellitus. However, although SU drugs that are most frequently used in Japan stimulate pancreatic β cells and thereby promote endogenous insulin secretion (see Non-Patent Document 3), they exhibit hypoglycemia as a side effect in some cases, and thus require attentions in uses in aged persons, persons with decreased renal function and cases of irregular eating. Furthermore, side effects such as body weight gain have also been reported. In addition, primary failure in which no effect is observed from the time of initial administration, or secondary failure in which a clinical effect is diminished during an administration period occurs in some cases (see Non-Patent Document 4), and thus development of an insulin secretagogue that remits these side effects and is less onerous against pancreatic β cells so as to not impair insulin secreting ability is desired.

As compounds having a condensed pyridine or condensed pyrimidine backbone, a compound having an activity of inhibiting Farnesoid X receptor (FXR) (Patent Document 1), compounds that are useful as therapeutic agents for metabolic diseases (Patent Documents 2 and 3), compounds that are useful as protein kinase inhibitors (Patent Documents 4 and 5), and a compound that is useful as a drug-resistant therapeutic agent (Patent Document 6) have been reported.

PRIOR ART DOCUMENTS

Patent Document

Patent Document 1: WO2009/127321
Patent Document 2: WO2007/115822
Patent Document 3: WO2006/077401
Patent Document 4: WO2005/113560
Patent Document 5: WO2009/070524
Patent Document 6: WO2004/065389

Non-Patent Documents

Non-Patent Document 1: J Clin Endocrinol Metab, May 2004, 89 (5): 2078-2084
Non-Patent Document 2: Regul Pept, 2004, 117 (2): 77-88
Non-Patent Document 3: The Lancet, Aug. 31, 1985, 2: 474-475
Non-Patent Document 4: The Lancet, Sep. 12, 1998, 352: 837-853

SUMMARY OF THE INVENTION

Technical Problem

The present invention aims at providing a compound that has an activity of promoting insulin secretion from pancreatic β cells and thus is useful as a prophylaxis and/or therapeutic drug for diseases caused by hyperglycemia such as diabetes mellitus.

Solution to Problem

The present inventors have conducted a search for a compound that promotes insulin secretion by using hamster pancreatic β cell strain HIT-T15 cells as part of studies for finding a compound having an activity of promoting insulin secretion and found that a condensed pyridine or condensed pyrimidine derivative represented by the formula (1) has an excellent action of promoting insulin secretion from pancreatic β cells and thus is useful as a prophylaxis or therapeutic drug for diabetes mellitus, and thereby completed the present invention.

Namely, the present invention relates to the inventions shown below:

[1] A compound represented by the following formula (1):

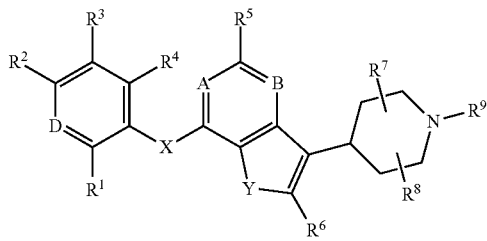

wherein
one of A and B represents a nitrogen atom and the other represents a nitrogen atom or $CR^{10}$ (wherein $R^{10}$ represents a hydrogen atom, a halogen atom, a $C_{1-6}$ alkyl group, a $C_{1-6}$ alkoxy group, an amino group or a nitro group);

D represents a nitrogen atom or $CR^{11}$ (wherein $R^{11}$ represents a hydrogen atom, a halogen atom, a $C_{1-6}$ alkyl group, a $C_{1-6}$ alkoxy group, an amino group or a nitro group);

X represents an oxygen atom, a sulfur atom or —(CH$_2$)n-N($R^{12}$)— (wherein $R^{12}$ represents a hydrogen atom or a $C_{1-6}$ alkyl group, and n represents 0 or 1);

Y represents an oxygen atom, a sulfur atom or —N($R^{13}$)— (wherein $R^{13}$ represents a hydrogen atom, a $C_{1-6}$ alkyl group or a substituted sulfonyl group);

$R^1$, $R^3$ and $R^4$ each independently represent a hydrogen atom, a halogen atom, a $C_{1-6}$ alkyl group, a $C_{1-6}$ alkoxy group, an amino group or a nitro group, or $R^1$ and $R^{12}$ may be together to form a nitrogen-containing heterocycle;

$R^2$ represents a hydrogen atom, —S(O)$R^{14}$, —S(O)$_2R^{15}$, —CO$_2R^{16}$, —CONR$^{17}R^{18}$ (wherein $R^{14}$ and $R^{15}$ each represent a $C_{1-6}$ alkyl group, a $C_{3-8}$ cycloalkyl group, a $C_{2-6}$ alkenyl group, a $C_{2-6}$ alkynyl group, an amino group, a mono($C_{1-6}$ alkyl)amino group or a di($C_{1-6}$ alkyl)amino group, $R^{16}$ represents a $C_{1-6}$ alkyl group, and $R^{17}$ and $R^{18}$ each independently represent a hydrogen atom or a $C_{1-6}$ alkyl group optionally having substituents) or a 5-10 membered heteroaryl group optionally having substituents;

$R^5$ represents a hydrogen atom, a halogen atom, a $C_{1-6}$ alkyl group, a $C_{1-6}$ alkoxy group, a $C_{1-6}$ alkylthio group or an amino group;

$R^6$ represents a hydrogen atom, a halogen atom, a $C_{1-6}$ alkyl group or an amino group;

$R^7$ and $R^8$ each independently represent a hydrogen atom or a $C_{1-6}$ alkyl group; and $R^9$ represents a $C_{1-6}$ alkyl group, —C(O)$R^{19}$, —C(S)$R^{20}$, —S(O)$_2R^{21}$, a $C_{6-10}$ aryl group optionally having substituents or a 5-10 membered heteroaryl group optionally having substituents (wherein $R^{19}$ represents a $C_{1-6}$ alkyl group, a $C_{1-6}$ alkoxy group, a halo $C_{1-6}$ alkyl group, a halo $C_{1-6}$ alkoxy group, a $C_{3-8}$ cycloalkyl group, a $C_{3-8}$ cycloalkoxy group, a halo $C_{3-8}$ cycloalkyl group, a halo $C_{3-8}$ cycloalkoxy group, a $C_{6-10}$ aryl group, a $C_{6-10}$ aryloxy group, a $C_{6-10}$ aryl $C_{1-6}$ alkoxy group, a 5-10 membered heteroaryl group optionally having substituents or a mono($C_{1-6}$ alkyl)amino group, $R^{20}$ and $R^{21}$ represent a $C_{1-6}$ alkyl group, a halo $C_{1-6}$ alkyl group, a $C_{3-8}$ cycloalkyl group, a mono($C_{1-6}$ alkyl)amino group, a $C_{6-10}$ aryl group optionally having substituents or a 5-10 membered heteroaryl group optionally having substituents), or a salt thereof, or a solvate of the compound or the salt.

[2] The compound according to the above-mentioned [1], wherein the nitrogen-containing heterocycle formed by $R^1$ and $R^{12}$ together is selected from the group consisting of the following formulas:

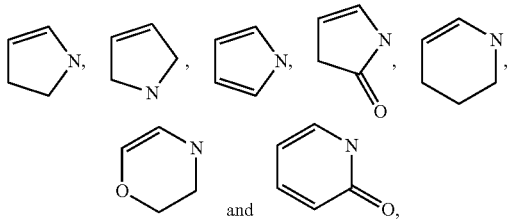

or a salt thereof, or a solvate of the compound or the salt.

[3] The compound according to the above-mentioned [1] or [2], which is selected from the following compound group, or a salt thereof, or a solvate of the compound or the salt:

tert-butyl 4-(4-{[2-fluoro-4-(methylsulfonyl)phenyl]amino}furo[3,2-d]pyrimidin-7-yl)piperidine-1-carboxylate, 7-[1-(5-chloropyrimidin-2-yl)piperidin-4-yl]-N-[2-fluoro-4-(methylsulfonyl)phenyl]furo[3,2-d]pyrimidine-4-amine, 7-[1-(5-ethylpyrimidin-2-yl)piperidin-4-yl]-N-[2-fluoro-4-(methylsulfonyl)phenyl]furo[3,2-d]pyrimidine-4-amine, N-[2-fluoro-4-(methylsulfonyl)phenyl]-7-[1-(5-fluoropyrimidin-2-yl)piperidin-4-yl]furo[3,2-d]pyrimidine-4-amine, 7-[1-(5-bromopyrimidin-2-yl)piperidin-4-yl]-N-[2-fluoro-4-(methylsulfonyl)phenyl]furo[3,2-d]pyrimidine-4-amine, N-[2-fluoro-4-(methylsulfonyl)phenyl]-7-{1-[5-(trifluoromethyl)pyridin-2-yl]piperidin-4-yl}furo[3,2-d]pyrimidine-4-amine, benzyl 4-(4-{[2-fluoro-4-(methylsulfonyl)phenyl]amino}furo[3,2-d]pyrimidin-7-yl)piperidine-1-carboxylate, isopropyl 4-(4-{[2-fluoro-4-(methylsulfonyl)phenyl]amino}furo[3,2-d]pyrimidin-7-yl)piperidine-1-carboxylate, ethyl 4-(4-{[2-fluoro-4-(methylsulfonyl)phenyl]amino}furo[3,2-d]pyrimidin-7-yl)piperidine-1-carboxylate, 7-(1-{[3,5-bis(trifluoromethyl)phenyl]sulfonyl}piperidin-4-yl)-N-[2-fluoro-4-(methylsulfonyl)phenyl]furo[3,2-d]pyrimidine-4-amine, 7-[1-(cyclopropylsulfonyl)piperidin-4-yl]-N-[2-fluoro-4-(methylsulfonyl)phenyl]furo[3,2-d]pyrimidine-4-amine, 7-[1-(cyclohexylsulfonyl)piperidin-4-yl]-N-[2-fluoro-4-(methylsulfonyl)phenyl]furo[3,2-d]pyrimidine-4-amine, N-[2-fluoro-4-(methylsulfonyl)phenyl]-7-[1-(thiophen-2-ylsulfonyl)piperidin-4-yl]furo[3,2-d]pyrimidine-4-amine, N-[2-fluoro-4-(methylsulfonyl)phenyl]-7-{1-[(4-methoxyphenyl)sulfonyl]piperidin-4-yl}furo[3,2-d]pyrimidine-4-amine, 7-[1-(butylsulfonyl)piperidin-4-yl]-N-[2-fluoro-4-(methylsulfonyl)phenyl]furo[3,2-d]pyrimidine-4-amine, N-[2-fluoro-4-(methylsulfonyl)phenyl]-7-{1-[(trichloromethyl)sulfonyl]piperidin-4-yl}furo[3,2-d]pyrimidine-4-amine, N-(tert-butyl)-4-(4-{[2-fluoro-4-(methylsulfonyl)phenyl]amino}furo[3,2-d]pyrimidin-7-yl)piperidine-1-carboxamide, N-(tert-butyl)-4-(4-{[2-fluoro-4-(methylsulfonyl)phenyl]amino}furo[3,2-d]pyrimidin-7-yl)piperidine-1-carbothioamide,

[4-(4-{[2-fluoro-4-(methylsulfonyl)phenyl]amino)furo[3,2-d]pyrimidin-7-yl)]piperidin-1-yl}(pyridin-2-yl)methanone,

[4-(4-{(2-fluoro-4-(methylsulfonyl)phenyl]amino)furo[3,2-d]pyrimidin-7-yl)piperidin-1-yl}(pyridin-3-yl)methanone, tert-butyl 4-{4-[3-fluoro-4-(methylsulfonyl)phenoxy]furo[3,2-d]pyrimidin-7-yl}piperidine-1-carboxylate, tert-butyl 4-{4-[(2-methylpyridin-3-yl)oxy]furo[3,2-d]pyrimidin-7-yl}piperidine-1-carboxylate, tert-butyl 4-(4-{[4-(methylsulfonyl)benzyl]amino}furo[3,2-d]pyrimidin-7-yl)piperidine-1-carboxylate, tert-butyl 4-{4-[5-(methylsulfonyl)indolin-1-yl]furo[3,2-d]pyrimidin-7-yl}piperidine-1-carboxylate, 7-[1-(5-ethylpyrimidin-2-yl)piperidin-4-yl]-4-[5-(methylsulfonyl)indolin-1-yl]furo[3,2-d]pyrimidine, 7-[1-(5-chloropyrimidin-2-yl)piperidin-4-yl]-4-[5-(methylsulfonyl)indolin-1-yl]furo[3,2-d]pyrimidine, tert-butyl 4-(4-{[2-fluoro-4-(methylsulfonyl)phenyl]amino}thieno[3,2-d]pyrimidin-7-yl)piperidine-1-carboxylate, tert-butyl 4-(4-{[2-fluoro-4-(methylsulfonyl)phenyl]amino}-5H-pyrrolo[3,2-d]pyrimidin-7-yl)piperidine-1-carboxylate, tert-butyl 4-(4-{[2-fluoro-4-(methylsulfonyl)phenyl]amino}-5-(methanesulfonyl)-5H-pyrrolo[3,2-d]pyrimidin-7-yl)piperidine-1-carboxylate, tert-butyl 4-(4-{[2-fluoro-4-(methylsulfonyl)phenyl]amino}-5-methyl-5H-pyrrolo[3,2-d]pyrimidin-7-yl)piperidine-1-carboxylate, N-[2-fluoro-4-(methylsulfonyl)phenyl]-7-{1-[5-(trifluoromethyl)pyrimidin-2-yl]piperidin-4-yl}furo[3,2-d]pyrimidine-4-amine, 2,2,2-trifluoroethyl 4-(4-{[2-fluoro-4-(methylsulfonyl)phenyl]amino}furo[3,2-d]pyrimidin-7-yl)piperidine-1-carboxylate, 1,1,1-trifluoro-2-methylpropan-2-yl 4-(4-{[2-fluoro-4-(methylsulfonyl)phenyl]amino}furo[3,2-d]pyrimidin-7-yl)piperidine-1-carboxylate, 4,4-difluorocyclohexyl(4-4-{[2-fluoro-4-(methylsulfonyl)phenyl]amino}furo[3,2-d]pyrimidin-7-yl)piperidine-1-carboxylate, neopentyl 4-(4-{[2-fluoro-4-(methylsulfonyl)phenyl]amino}furo[3,2-d]pyrimidin-7-yl)piperidine-1-carboxylate, 2,2,2-trichloroethyl 4-(4-{[2-fluoro-4-(methylsulfonyl)phenyl]amino}furo[3,2-d]pyrimidin-7-yl)piperidine-1-carboxylate, phenyl 4-(4-{[2-fluoro-4-(methylsulfonyl)phenyl]amino}furo[3,2-d]pyrimidin-7-yl)piperidine-1-carboxylate, 1-[4-(4-{[2-fluoro-4-(methylsulfonyl)phenyl]amino}furo[3,2-d]pyrimidin-7-yl)piperidin-1-yl]-3,3-dimethylbutan-1-one, tert-butyl 4-(4-{[2-fluoro-4-(methylsulfonyl)phenyl](methyl)amino}furo[3,2-d]pyrimidin-7-yl)piperidine-1-carboxylate, tert-butyl 4-(4-{4-(methylsulfonyl)phenoxy}furo[3,2-d]pyrimidin-7-yl)piperidine-1-carboxylate, and tert-butyl 4-{4-[4-(1H-tetrazol-1-yl)phenoxy]furo[3,2-d]pyrimidin-7-yl}piperidine-1-carboxylate.

[4] A compound represented by the following formula (1):

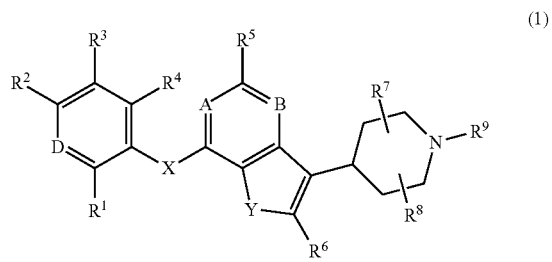

wherein
one of A and B represents a nitrogen atom and the other represents a nitrogen atom or $CR^{10}$ (wherein $R^{10}$ represents a hydrogen atom, a halogen atom, a $C_{1-6}$ alkyl group, a $C_{1-6}$ alkoxy group, an amino group or a nitro group);

D represents a nitrogen atom or $CR^{11}$ (wherein $R^{11}$ represents a hydrogen atom, a halogen atom, a $C_{1-6}$ alkyl group, a $C_{1-6}$ alkoxy group, an amino group or a nitro group);

X represents an oxygen atom, a sulfur atom or —$(CH_2)n$-$N(R^{12})$— (wherein $R^{12}$ represents a hydrogen atom or a $C_{1-6}$ alkyl group, and n represents 0 or 1);

Y represents an oxygen atom, a sulfur atom or —$N(R^{13})$— (wherein $R^{13}$ represents a hydrogen atom, a $C_{1-6}$ alkyl group or a substituted sulfonyl group);

$R^1$, $R^3$ and $R^4$ each independently represent a hydrogen atom, a halogen atom, a $C_{1-6}$ alkyl group, a $C_{1-6}$ alkoxy group, an amino group or a nitro group;

$R^2$ represents a hydrogen atom, —$S(O)R^{14}$, —$S(O)_2R^{15}$, —$CO_2R^{16}$, —$CONR^{17}R^{18}$ (wherein $R^{14}$ and $R^{16}$ each represent a $C_{1-6}$ alkyl group, a $C_{3-8}$ cycloalkyl group, a $C_{2-6}$ alkenyl group, a $C_{2-6}$ alkynyl group, an amino group, a mono($C_{1-6}$ alkyl)amino group or a di($C_{1-6}$ alkyl)amino group, $R^{16}$ represents a $C_{1-6}$ alkyl group, and $R^{17}$ and $R^{18}$ each independently represent a hydrogen atom or a $C_{1-6}$ alkyl group optionally having substituents) or a 5-10 membered heteroaryl group optionally having substituents;

$R^5$ represents a hydrogen atom, a halogen atom, a $C_{1-6}$ alkyl group, a $C_{1-6}$ alkoxy group, a $C_{1-6}$ alkylthio group or an amino group;

$R^6$ represents a hydrogen atom, a halogen atom, a $C_{1-6}$ alkyl group or an amino group;

$R^7$ and $R^8$ each independently represent a hydrogen atom or a $C_{1-6}$ alkyl group;

$R^9$ represents a $C_{1-6}$ alkyl group, —$C(O)R^{19}$, —$C(S)R^{20}$, —$S(O)_2R^{21}$, a $C_{6-10}$ aryl group optionally having substituents or a 5-10 membered heteroaryl group optionally having substituents (wherein $R^{19}$ represents a $C_{1-6}$ alkyl group, a $C_{1-6}$ alkoxy group, a halo $C_{1-6}$ alkyl group, a halo $C_{1-6}$ alkoxy group, a $C_{3-8}$ cycloalkyl group, a halo $C_{3-8}$ cycloalkyl group, a $C_{3-8}$ cycloalkoxy group, a halo $C_{3-8}$ cycloalkoxy group, a $C_{6-10}$ aryl group, a $C_{6-10}$ aryloxy group, a $C_{6-10}$ aryl $C_{1-6}$ alkoxy group, a 5-10 membered heteroaryl group optionally having substituents or a mono($C_{1-6}$ alkyl)amino group, $R^{20}$ and $R^{21}$ each represent a $C_{1-6}$ alkyl group, a halo $C_{1-6}$ alkyl group, a $C_{3-8}$ cycloalkyl group, a mono($C_{1-6}$ alkyl)amino group, a $C_{6-10}$ aryl group optionally having substituents or a 5-10 membered heteroaryl group optionally having substituents), or a salt thereof, or a solvate of the compound or the salt.

[5] The compound according to the above-mentioned [4], which is selected from the following compound group, or a salt thereof, or a solvate of the compound or the salt:

tert-butyl 4-(4-{[2-fluoro-4-(methylsulfonyl)phenyl]amino}furo[3,2-d]pyrimidin-7-yl)piperidine-1-carboxylate, 7-[1-(5-chloropyrimidin-2-yl)piperidin-4-yl]-N-[2-fluoro-4-(methylsulfonyl)phenyl]furo[3,2-d]pyrimidine-4-amine,
7-[1-(5-ethylpyrimidin-2-yl)piperidin-4-yl]-N-[2-fluoro-4-(methylsulfonyl)phenyl]furo[3,2-d]pyrimidine-4-amine,
N-[2-fluoro-4-(methylsulfonyl)phenyl]-7-[1-(5-fluoropyrimidin-2-yl)piperidin-4-yl]furo[3,2-d]pyrimidine-4-amine,
7-[1-(5-bromopyrimidin-2-yl)piperidin-4-yl]-N-[2-fluoro-4-(methylsulfonyl)phenyl]furo[3,2-d]pyrimidine-4-amine,
N-[2-fluoro-4-(methylsulfonyl)phenyl]-7-{1-[5-(trifluoromethyl)pyridin-2-yl]piperidin-4-yl}furo[3,2-d]pyrimidine-4-amine,
benzyl 4-(4-{[2-fluoro-4-(methylsulfonyl)phenyl]amino}furo[3,2-d]pyrimidin-7-yl)piperidine-1-carboxylate,
isopropyl 4-(4-{[2-fluoro-4-(methylsulfonyl)phenyl]amino}furo[3,2-d]pyrimidin-7-yl)piperidine-1-carboxylate,
ethyl 4-(4-{[2-fluoro-4-(methylsulfonyl)phenyl]amino}furo[3,2-d]pyrimidin-7-yl)piperidine-1-carboxylate,
7-(1-{[3,5-bis(trifluoromethyl)phenyl]sulfonyl}piperidin-4-yl)-N-[2-fluoro-4-(methylsulfonyl)phenyl]furo[3,2-d]pyrimidine-4-amine,
7-[1-(cyclopropylsulfonyl)piperidin-4-yl]-N-[2-fluoro-4-(methylsulfonyl)phenyl]furo[3,2-d]pyrimidine-4-amine,
7-[1-(cyclohexylsulfonyl)piperidin-4-yl]-N-[2-fluoro-4-(methylsulfonyl)phenyl]furo[3,2-d]pyrimidine-4-amine,
N-[2-fluoro-4-(methylsulfonyl)phenyl]-7-[1-(thiophen-2-ylsulfonyl)piperidin-4-yl]furo[3,2-d]pyrimidine-4-amine,
N-[2-fluoro-4-(methylsulfonyl)phenyl]-7-{1-[(4-methoxyphenyl)sulfonyl]piperidin-4-yl}furo[3,2-d]pyrimidine-4-amine,
7-[1-(butylsulfonyl)piperidin-4-yl]-N-[2-fluoro-4-(methylsulfonyl)phenyl]furo[3,2-d]pyrimidine-4-amine,
N-[2-fluoro-4-(methylsulfonyl)phenyl]-7-{1-[(trichloromethyl)sulfonyl]piperidin-4-yl}furo[3,2-d]pyrimidine-4-amine,
N-(tert-butyl)-4-(4-{[2-fluoro-4-(methylsulfonyl)phenyl]amino}furo[3,2-d]pyrimidin-7-yl)piperidine-1-carboxamide,
N-(tert-butyl)-4-(4-{[2-fluoro-4-(methylsulfonyl)phenyl]amino}furo[3,2-d]pyrimidin-7-yl)piperidine-1-carbothioamide,
[4-(4-{[2-fluoro-4-(methylsulfonyl)phenyl]amino}furo[3,2-d]pyrimidin-7-yl)piperidin-1-yl](pyridin-2-yl)methanone,
[4-(4-{[2-fluoro-4-(methylsulfonyl)phenyl]amino}furo[3,2-d]pyrimidin-7-yl)piperidin-1-yl](pyridin-3-yl)methanone,
tert-butyl 4-{4-[3-fluoro-4-(methylsulfonyl)phenoxy]furo[3,2-d]pyrimidin-7-yl}piperidine-1-carboxylate,
tert-butyl 4-{4-[(2-methylpyridin-3-yl)oxy]furo[3,2-d]pyrimidin-7-yl}piperidine-1-carboxylate,
tert-butyl 4-(4-{[4-(methylsulfonyl)benzyl]amino}furo[3,2-d]pyrimidin-7-yl)piperidine-1-carboxylate,
tert-butyl 4-(4-{[2-fluoro-4-(methylsulfonyl)phenyl]amino}thieno[3,2-d]pyrimidin-7-yl)piperidine-1-carboxylate,
tert-butyl 4-(4-{[2-fluoro-4-(methylsulfonyl)phenyl]amino}-5H-pyrrolo[3,2-d]pyrimidin-7-yl)piperidine-1-carboxylate,
tert-butyl 4-(4-{[2-fluoro-4-(methylsulfonyl)phenyl]amino}-5-(methanesulfonyl)-5H-pyrrolo[3,2-d]pyrimidin-7-yl)piperidine-1-carboxylate,
tert-butyl 4-(4-{[2-fluoro-4-(methylsulfonyl)phenyl]amino}-5-methyl-5H-pyrrolo[3,2-d]pyrimidin-7-yl)piperidine-1-carboxylate,
N-[2-fluoro-4-(methylsulfonyl)phenyl]-7-{1-[5-(trifluoromethyl)pyrimidin-2-yl]piperidin-4-yl}furo[3,2-d]pyrimidine-4-amine,
2,2,2-trifluoroethyl 4-(4-{[2-fluoro-4-(methylsulfonyl)phenyl]amino}furo[3,2-d]pyrimidin-7-yl)piperidine-1-carboxylate,
1,1,1-trifluoro-2-methylpropan-2-yl 4-(4-{[2-fluoro-4-(methylsulfonyl)phenyl]amino}furo[3,2-d]pyrimidin-7-yl)piperidine-1-carboxylate, 4,4-difluorocyclohexyl 4-(4-{[2-fluoro-4-(methylsulfonyl)phenyl]amino}furo[3,2-d]pyrimidin-7-yl)piperidine-1-carboxylate,
neopentyl 4-(4-{[2-fluoro-4-(methylsulfonyl)phenyl]amino}furo[3,2-d]pyrimidin-7-yl)piperidine-1-carboxylate,
2,2,2-trichloroethyl 4-(4-{[2-fluoro-4-(methylsulfonyl)phenyl]amino}furo[3,2-d]pyrimidin-7-yl)piperidine-1-carboxylate,
phenyl 4-(4-{[2-fluoro-4-(methylsulfonyl)phenyl]amino}furo[3,2-d]pyrimidin-7-yl)piperidine-1-carboxylate,
1-[4-(4-{[2-fluoro-4-(methylsulfonyl)phenyl]amino}furo[3,2-d]pyrimidin-7-yl)piperidin-1-yl]-3,3-dimethylbutan-1-one,
tert-butyl 4-(4-{[2-fluoro-4-(methylsulfonyl)phenyl](methyl)amino}furo[3,2-d]pyrimidin-7-yl)piperidine-1-carboxylate,
tert-butyl 4-(4-{4-(methylsulfonyl)phenoxy}furo[3,2-d]pyrimidin-7-yl)piperidine-1-carboxylate, and
tert-butyl 4-{4-[4-(1H-tetrazol-1-yl)phenoxy]furo[3,2-d]pyrimidin-7-yl}piperidine-1-carboxylate.

[6] A pharmaceutical composition containing the compound according to any of the above-mentioned [1] to [5] or a salt thereof, or a solvate of the compound or the salt, and a pharmaceutically acceptable carrier.

[7] An insulin secretagogue containing the compound according to any of the above-mentioned [1] to [5] or a salt thereof, or a solvate of the compound or the salt as an active ingredient.

[8] A hypoglycemic agent containing the compound according to any of the above-mentioned [1] to [5] or a salt thereof, or a solvate of the compound or the salt as an active ingredient.

[9] A prophylaxis and/or therapeutic agent for diabetes mellitus containing the compound according to any of the above-mentioned [1] to [5] or a salt thereof, or a solvate of the compound or the salt as an active ingredient.

[10] A method for promoting insulin secretion, including administering an effective amount of the compound according to any of the above-mentioned [1] to [5] or a salt thereof, or a solvate of the compound or the salt, to the subject in need thereof.

[11] A method for decreasing blood glucose, including administering an effective amount of the compound according to any of the above-mentioned [1] to [5] or a salt thereof, or a solvate of the compound or the salt.

[12] A method for the prophylaxis and/or therapy of diabetes mellitus, including administering an effective amount of the compound according to any of the above-mentioned [1] to [5] or a salt thereof, or a solvate of the compound or the salt.

[13] The compound according to any of the above-mentioned [1] to [5] or a salt thereof, or a solvate of the compound or the salt, for promoting insulin secretion.

[14] The compound according to any of the above-mentioned [1] to [5] or a salt thereof, or a solvate of the compound or the salt, for decreasing blood glucose.

[15] The compound according to any of the above-mentioned [1] to [5] or a salt thereof, or a solvate of the compound or the salt, for the prophylaxis and/or therapy of diabetes mellitus.

[16] Use of the compound according to any of the above-mentioned [1] to [5] or a salt thereof, or a solvate of the compound or the salt, in the production of an insulin secretagogue, a hypoglycemic agent or a prophylaxis and/or therapeutic agent for diabetes mellitus.

Effects of the Invention

The condensed pyridine or condensed pyrimidine derivative or a salt thereof, or a solvate of the compound or the salt of the present invention is a low molecular compound that has an action of strongly promoting insulin secretion from pancreatic β cells and can be administered orally, and is useful as a prophylaxis and/or therapeutic agent for diseases that are caused by hyperglycemia such as diabetes mellitus in mammals including human.

EMBODIMENTS FOR CARRYING OUT THE INVENTION

In the present specification, examples of the "halogen atom" may include a fluorine atom, a chlorine atom, a bromine atom or an iodine atom, and the like.

In the present specification, the "$C_{1-6}$ alkyl group" means a straight chain or branched chain alkyl group having 1 to 6 carbons, and examples thereof may include a methyl group, an ethyl group, an n-propyl group, an isopropyl group, an n-butyl group, an isobutyl group, a tert-butyl group, an n-pentyl group, a 2-methylbutyl group, a 2,2-dimethylpropyl group, an n-hexyl group and the like.

In the present specification, the "halo $C_{1-6}$ alkyl group" is a $C_{1-6}$ alkyl group substituted with identical or different halogen atoms of one to the maximum number that allows substitution, and examples thereof may include a monofluoromethyl group, a difluoromethyl group, a trifluoromethyl group, a monochloromethyl group, a dichloromethyl group, a trichloromethyl group, a monobromomethyl group, a monoiodomethyl group, a 2,2,2-trichloroethyl group, a 2,2,2-trifluoroethyl group, a 1,1,1-trifluoro-2-methylpropan-2-yl group and the like.

In the present specification, examples of the "$C_{3-8}$ cycloalkyl group" may include monocyclic, polycyclic or condensed cyclic cycloalkyl groups having 3 to 8 carbons, preferably 3 to 6 carbons. Examples of such cycloalkyl groups may include a cyclopropyl group, a cyclobutyl group, a cyclopentyl group, a cyclohexyl group, a cycloheptyl group, a cyclooctyl group and the like.

In the present specification, the "halo $C_{3-8}$ cycloalkyl group" is a $C_{3-8}$ cycloalkyl group substituted with identical or different halogen atoms of one to the maximum number that allows substitution, and examples thereof may include a fluorocyclopropyl group, a chlorocyclobutyl group, a bromocyclopentyl group, a difluorocyclohexyl group, a dichlorocycloheptyl group, a dibromocyclooctyl group and the like.

In the present specification, examples of the "$C_{2-6}$ alkenyl group" may include a vinyl group, a prop-1-en-1-yl group (a 1-propenyl group), a prop-2-en-1-yl group (an allyl group), an isopropenyl group, a but-1-en-1-yl group, a but-2-en-1-yl group (a crotyl group), a but-3-en-1-yl group, a 2-methylprop-2-en-1-yl group, a 1-methylprop-2-en-1-yl group, a pent-1-en-1-yl group, a pent-2-en-1-yl group, a pent-3-en-1-yl group, a pent-4-en-1-yl group, a 3-methylbut-2-en-1-yl group, a 3-methylbut-3-en-1-yl group, a hex-1-en-1-yl group, a hex-2-en-1-yl group, a hex-3-en-1-yl group, a hex-4-en-1-yl group, a hex-5-en-1-yl group, a 4-methylpent-3-en-1-yl group and the like.

In the present specification, examples of the "$C_{2-6}$ alkynyl group" may include an ethynyl group, a prop-1-yn-1-yl group, a prop-2-yn-1-yl group (a propargyl group), a but-1-yn-1-yl group, a but-3-yn-1-yl group, a 1-methylprop-2-yn-1-yl group, a pent-1-yn-1-yl group, a pent-4-yn-1-yl group, a hex-1-yn-1-yl group, a hex-5-yn-1-yl group and the like.

In the present specification, examples of the "$C_{1-6}$ alkoxy group" may include a methoxy group, an ethoxy group, an n-propoxy group, an isopropoxy group, an n-butoxy group, an isobutoxy group, a sec-butoxy group, a tert-butoxy group, an n-pentoxy group, an isopentoxy group, a neopentoxy group, an n-hexyloxy group, an isohexyloxy group and the like.

In the present specification, examples of the "halo $C_{1-6}$ alkoxy group" may include a monofluoromethoxy group, a difluoromethoxy group, a trifluoromethoxy group, a monochloromethoxy group, a dichloromethoxy group, a trichloromethoxy group, a monobromomethoxy group, a monoiodomethoxy group, a 2,2,2-trichloroethoxy group, a 2,2,2-trifluoroethoxy group, a 1,1,1-trifluoro-2-methylpropan-2-yloxy group and the like.

In the present specification, examples of the "$C_{3-8}$ cycloalkoxy group" may include a cyclopropoxy group, a cyclobutoxy group, a cyclopentoxy group, a cyclohexyloxy group, a cycloheptyloxy group, a cyclooctyloxy group and the like.

In the present specification, examples of the "halo $C_{3-8}$ cycloalkoxy group" may include a fluorocyclopropoxy group, a chlorocyclobutoxy group, a bromocyclopentoxy group, a difluorocyclohexyloxy group, a dichlorocycloheptyloxy group, a dibromocyclooctyloxy group and the like.

In the present specification, examples of the "$C_{1-6}$ alkylthio group" may include a methylthio group, an ethylthio group, an n-propylthio group, an isopropylthio group, a n-butylthio group, an isobutylthio group, a sec-butylthio group, a tert-butylthio group, an n-pentylthio group, an isopentylthio group, a neopentylthio group, an n-hexylthio group, an isohexylthio group and the like.

In the present specification, the "mono($C_{1-6}$ alkyl)amino group" means a group in which one alkyl group mentioned above is bound to a nitrogen atom, and examples thereof may include a methylamino group, an ethylamino group, a propylamino group, an isopropylamino group, a butylamino group, a sec-butylamino group, a tert-butylamino group, an n-pentylamino group, an isopentylamino group, a neopentylamino group, an n-hexylamino group, an isohexylamino group and the like.

In the present specification, the "di($C_{1-6}$ alkyl)amino group" means a group in which two identical or different alkyl groups mentioned above are bound to a nitrogen atom, and examples thereof may include a dimethylamino group, a methylethylamino group, a diethylamino group, a methylpropylamino group, an ethylpropylamino group, a dipropylamino group, a diisopropylamino group, a dibutylamino group and the like.

In the present specification, examples of the "$C_{6-10}$ aryl group" may include a phenyl group, a naphthyl group, an azulenyl group and the like.

In the present specification, examples of the "$C_{6-10}$ aryloxy group" may include a phenoxy group, a naphthoxy group, an azulenyloxy group and the like.

In the present specification, the "substituted sulfonyl group" means "a $C_{1-6}$ alkylsulfonyl group" wherein the alkyl group is bound through sulfonyl ($-SO_2-$), "a halo $C_{1-6}$ alkylsulfonyl group" wherein the haloalkyl group is bound through a sulfonyl group, "a $C_{3-8}$ cycloalkylsulfonyl group" wherein the $C_{3-8}$ cycloalkyl group is bound through sulfonyl, "a $C_{2-6}$ alkenylsulfonyl group" wherein the $C_{2-6}$ alkenyl group is bound through sulfonyl, "a $C_{2-6}$ alkynylsulfonyl group" wherein the $C_{2-6}$ alkynyl group is bound through sulfonyl, "a sulfamoyl group" wherein the amino group is bound through sulfonyl, "a mono($C_{1-6}$ alkyl) sulfamoyl group" or "a di($C_{1-6}$ alkyl)sulfamoyl group" wherein the mono($C_{1-6}$ alkyl)amino group or di($C_{1-6}$ alkyl)amino group is bound through sulfonyl, "a $C_{6-10}$ arylsulfonyl group" wherein the aryl group is bound through sulfonyl, and the like.

Examples of the "$C_{1-6}$ alkylsulfonyl group" may include a methylsulfonyl group, an ethylsulfonyl group, an n-propylsulfonyl group, an isopropylsulfonyl group, an n-butylsulfonyl group, an isobutylsulfonyl group, a sec-butylsulfonyl group, a tert-butylsulfonyl group, an n-pentylsulfonyl group, an isopentylsulfonyl group, a neopentylsulfonyl group, a 2-methylbutylsulfonyl group, a 1-methylbutylsulfonyl group, an 1-ethylpropylsulfonyl group, a 2,2-dimethylpropylsulfonyl group, an n-hexylsulfonyl group, a 4-methylpentylsulfonyl group, a 3-methylpentylsulfonyl group, a 2-methylpentylsulfonyl group, a 1-methylpentylsulfonyl group, a 3,3-dimethylbutylsulfonyl group, a 2,2-dimethylbutylsulfonyl group, a 1,1-dimethylbutylsulfonyl group, a 1,2-dimethylbutylsulfonyl group, a 1,3-dimethylbutylsulfonyl group, a 2,3-dimethylbutylsulfonyl group, an 1-ethylbutylsulfonyl group, an 2-ethylbutylsulfonyl group and the like.

Examples of the "halo $C_{1-6}$ alkylsulfonyl group" may include a fluoromethylsulfonyl group, a difluoromethylsulfonyl group, a trifluoromethylsulfonyl group, a chloromethylsulfonyl group, a bromomethylsulfonyl group, an iodomethylsulfonyl group, a 2,2,2-trifluoroethylsulfonyl group and the like.

Examples of the "$C_{3-8}$ cycloalkylsulfonyl group" may include a cyclopropylsulfonyl group, a cyclobutylsulfonyl group, a cyclopentylsulfonyl group, a cyclohexylsulfonyl group, a cycloheptylsulfonyl group, a cyclooctylsulfonyl group and the like.

Examples of the "$C_{2-6}$ alkenylsulfonyl group" may include a vinylsulfonyl group, a propenylsulfonyl group, an allylsulfonyl group, a crotylsulfonyl group and the like.

Examples of the "$C_{2-6}$ alkynylsulfonyl group" may include an ethynylsulfonyl group, a propargylsulfonyl group and the like.

Examples of the "mono($C_{1-6}$ alkyl)sulfamoyl group" may include a methylsulfamoyl group, an ethylsulfamoyl group, a propylsulfamoyl group, an isopropylsulfamoyl group, a butylsulfamoyl group, a sec-butylsulfamoyl group, a tert-butylsulfamoyl group, a pentylsulfamoyl group, a hexylsulfamoyl group and the like.

Examples of the "di($C_{1-6}$ alkyl)sulfamoyl group" may include a dimethylsulfamoyl group, a methylethylsulfamoyl group, a diethylsulfamoyl group, a dipropylsulfamoyl group, a diisopropylsulfamoyl group, a dibutylsulfamoyl group and the like.

Examples of the "$C_{6-10}$ arylsulfonyl group" may include a phenylsulfonyl group, a naphthylsulfonyl group, an azulenylsulfonyl group and the like.

In the present specification, the "nitrogen-containing heterocycle" means a 5- or 6-membered saturated or unsaturated heterocycle having at least one nitrogen atom and further optionally having an oxygen atom, and examples thereof may include 2,3-dihydro-1H-pyrrole(2-pyrroline), 2,5-dihydro-1H-pyrrole(3-pyrroline), 3-pyrrolin-2-one, 1H-pyrrole, 2-pyrrolin-5-one, 1,2,3,4-tetrahydropyridine, 1,2,3,4-tetrahydropyridin-2-one, 1,2,3,6-tetrahydropyridine, 3,4-dihydro-2H-1,4-oxazine, 2,3-dihydro-4H-1,4-oxazin-3-one, 1,2-dihydropyridin-2-one and the like.

In the present specification, the "5-10 membered heteroaryl group" means a 5- to 10-membered monocyclic, polycyclic or condensed cyclic aromatic heterocycle group containing 1 to 4 heteroatoms selected from an oxygen atom, a sulfur atom and a nitrogen atom, and examples thereof may include a furyl group, a thienyl group, a pyrrolyl group, an oxazolyl group, an isoxazolyl group, a thiazolyl group, an isothiazolyl group, an imidazolyl group, a pyrazolyl group, an oxadiazolyl group, a thiadiazolyl group, triazolyl group, a tetrazolyl group, a pyridyl group, a pyrimidyl group, a pyrazinyl group, a pyridazinyl group, a benzofuranyl group, an isobenzofuranyl group, a benzothienyl group, an indolyl group, an isoindolyl group, an indazolyl group, a benzimidazolyl group, a benzoxazolyl group, a benzisoxazolyl group, a benzothiazolyl group, a benzisothiazolyl group, a benzoxadiazolyl group, a benzothiadiazolyl group, a benzotriazolyl group, a quinolyl group, an isoquinolyl group, a cinnolinyl group, a quinazolinyl group, a quinoxalinyl group, a phthalazinyl group, a naphthylidinyl group, a purinyl group, a pteridinyl group, a furopyridyl group, a thienopyridyl group, a pyrrolopyridyl group, a oxazolopyridyl group, a thiazolopyridyl group, an imidazopyridyl group and the like.

In the present specification, the "$C_{6-10}$ aryl $C_{1-6}$ alkoxy group" means a group in which the above-mentioned $C_{1-6}$ alkoxy group is bound to a phenyl group, a naphthyl group, an azulenyl group or the like. Examples thereof may include a phenyl-$C_{1-6}$ alkoxy group, a naphthyl-$C_{1-6}$ alkoxy group and an azulenyl-$C_{1-6}$ alkoxy group. More specific examples may include a benzyloxy group, a phenetyloxy group, a naphthylmethyloxy group and the like.

In the present specification, examples of the "substituents" in the $C_{1-6}$ alkyl group optionally having substituents may include a halogen atom, a $C_{3-8}$ cycloalkyl group, a $C_{1-6}$ alkoxy group, a mono($C_{1-6}$ alkyl)amino group, a di($C_{1-6}$ alkyl)amino group, a di($C_{2-6}$ alkenyl)amino group, a mono($C_{3-8}$ cycloalkyl)amino group, a $C_{2-7}$ alkoxycarbonyl group, an amino group, a carboxyl group, a cyano group, a carbamoyl group, a sulfamoyl group, a hydroxyl group, a nitro group and the like. One to four of these substituents may be possessed. Meanwhile, the carbon number ($C_{2-7}$) in the alkoxycarbonyl group represents a number including the carbonyl carbon.

In the present specification, examples of the "substituents" in the $C_{6-10}$ aryl group optionally having substituents and the 5-10 membered heteroaryl group optionally having substituents may include a halogen atom, a $C_{1-6}$ alkyl group, a $C_{3-8}$ cycloalkyl group, a halo $C_{1-6}$ alkyl group, $C_{2-6}$ alkenyl group, a $C_{2-6}$ alkynyl group, a $C_{1-6}$ alkoxy group, a mono($C_{1-6}$ alkyl) amino group, a di($C_{1-6}$ alkyl)amino group, a di($C_{2-6}$ alkenyl) amino group, a mono($C_{3-8}$ cycloalkyl)amino group, a dioxaboranyl group, a morpholino group, a piperidino group, an oxadiazolyl group, a $C_{2-7}$ alkoxycarbonyl group, an amino group, a carboxyl group, a cyano group, a carbamoyl group, a sulfamoyl group, a hydroxyl group, a nitro group and the like. One to four of these substituents may be possessed. Furthermore, these substituents may further have substituents.

In the formula (1), as the halogen atom in $R^1$, $R^3$ and $R^4$, a chlorine atom and a fluorine atom are preferable, and a fluorine atom is more preferable.

In the general formula (1), as the $C_{1-6}$ alkyl group in $R^1$, $R^3$ and $R^4$, a $C_{1-4}$ alkyl group is preferable, and a methyl group and an ethyl group are more preferable.

In the formula (1), as the $C_{6-10}$ heteroaryl group optionally having substituents in $R^9$, a pyridyl group and a pyrimidinyl group are preferable. Furthermore, as the substituent parts, halogen atoms (a fluorine atom, a chlorine atom, a bromine atom and the like), $C_{1-6}$ alkyl groups (a methyl group, an ethyl group and the like) and halo $C_{1-6}$ alkyl groups (a trifluoromethyl group and the like) are preferable.

In the formula (1), as the nitrogen-containing heterocycle formed by $R^1$ and $R^{12}$ together, a heterocycle selected from the following formulas:

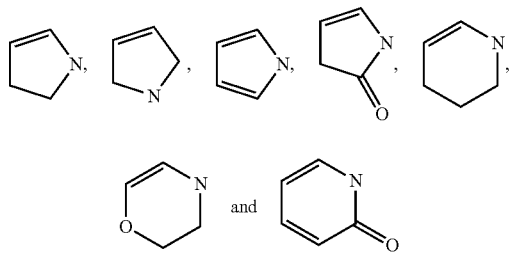

is preferable.

In the formula (1), as the $C_{1-6}$ alkyl group in $R^{13}$, a $C_{1-4}$ alkyl group is preferable, and a methyl group and an ethyl group are more preferable.

In the formula (1), as the substituted sulfonyl group in $R^{13}$, a $C_{1-6}$ alkylsulfonyl group is preferable, and a methylsulfonyl group and an ethylsulfonyl group are more preferable.

In the formula (1), as the $C_{1-6}$ alkyl group in $R^{15}$, a $C_{1-4}$ alkyl group is preferable, and a methyl group and an ethyl group are more preferable.

In the formula (1), as the $C_{1-6}$ alkyl group in $R^{19}$, a $C_{1-5}$ alkyl group is preferable, a methyl group, an ethyl group, an isopropyl group, a tert-butyl group and a 2,2-dimethylpropyl group are preferable, and a 2,2-dimethylpropyl group is more preferable.

In the formula (1), as the $C_{1-6}$ alkoxy group in $R^{19}$, a $C_{1-5}$ alkoxy group is preferable, and a methoxy group, an ethoxy group, an isopropoxy group, a tert-butoxy group and a 2,2-dimethylpropoxy group are more preferable.

In the formula (1), as the halo $C_{1-6}$ alkyl group in $R^{19}$, a halo $C_{1-5}$ alkyl group is preferable, and a 2,2,2-trichloroethyl group, a 2,2,2-trifluoroethyl group and a 1,1,1-trifluoro-2-methylpropan-2-yl group are more preferable.

In the formula (1), as the halo $C_{1-6}$ alkoxy group in $R^{19}$, a halo $C_{1-5}$ alkoxy group is preferable, and a 2,2,2-trichloroethoxy group, a 2,2,2-trifluoroethoxy group and a 1,1,1-trifluoro-2-methylpropan-2-yloxy group are more preferable.

In the formula (1), as the $C_{3-8}$ cycloalkyl group in $R^{19}$, a cyclopropyl group, a cyclobutyl group, a cyclopentyl group and a cyclohexyl group are preferable.

In the formula (1), as the $C_{3-8}$ cycloalkoxy group in $R^{19}$, a cyclopropoxy group, a cyclobutoxy group, a cyclopentoxy group and a cyclohexyloxy group are preferable.

In the formula (1), as the halo $C_{3-8}$ cycloalkyl group in $R^{19}$, a fluorocyclopropyl group, a chlorocyclobutyl group, a bromocyclopentyl group, a difluorocyclohexyl group, a dichlorocycloheptyl group and a dibromocyclooctyl group are preferable.

In the formula (1), as the halo $C_{3-8}$ cycloalkoxy group in $R^{19}$, a fluorocyclopropoxy group, a chlorocyclobutoxy group, a bromocyclopentoxy group, a difluorocyclohexyloxy group, a dichlorocycloheptyloxy group and a dibromocyclooctyloxy group are preferable, and a difluorocyclohexyloxy group is more preferable.

In the formula (1), as the $C_{6-10}$ aryl group in $R^{19}$, a phenyl group is preferable.

In the formula (1), as the $C_{6-10}$ aryloxy group in $R^{19}$, a phenoxy group is preferable.

In the formula (1), as the $C_{6-10}$ aryl $C_{1-6}$ alkoxy group in $R^{19}$, a phenyl $C_{1-6}$ alkoxy group is preferable, and a benzyloxy group is more preferable.

In the formula (1), as the 5-10 membered heteroaryl group optionally having substituents in $R^{19}$, a pyridyl group and a pyrimidyl group are preferable.

In the formula (1), as the mono($C_{1-6}$ alkyl)amino group in $R^{19}$, a mono($C_{1-4}$ alkyl)amino group is preferable, and an ethylamino group and a tert-butylamino group are more preferable.

In the formula (1), as the mono($C_{1-6}$ alkyl)amino group in $R^{20}$, a mono($C_{1-4}$ alkyl)amino group is preferable, and an ethylamino group and a tert-butylamino group are more preferable.

In the formula (1), as the $C_{1-6}$ alkyl group in $R^{21}$, a $C_{1-4}$ alkyl group is preferable, and a methyl group and an n-butyl group are more preferable.

In the formula (1), as the halo $C_{1-6}$ alkyl group in $R^{21}$, a halo $C_{1-4}$ alkyl group is preferable, and a trichloromethyl group and a trifluoromethyl group are more preferable.

In the formula (1), as the $C_{3-6}$ cycloalkyl group in $R^{21}$, a $C_{3-6}$ cycloalkyl group is preferable, and a cyclopropyl group and cyclohexyl group are preferable.

In the formula (1), as the $C_{6-10}$ aryl group optionally having substituents in $R^{21}$, a phenyl group optionally having substituents is preferable. As the substituent parts, halo $C_{1-6}$ alkyl groups (a trifluoromethyl group and the like), $C_{1-6}$ alkoxy groups (a methoxy group and the like) are preferable.

In the formula (1), as the $C_{6-10}$ heteroaryl group optionally having substituents in $R^{21}$, a thienyl group is preferable.

In the formula (1), as A and B, the case when A and B are nitrogen atoms, the case when A is a nitrogen atom and B is CH, and the case when A is CH and B is a nitrogen atom are more preferable, and the case when A and B are nitrogen atoms is even more preferable.

In the formula (1), as D, a nitrogen atom, CH or C-halogen is preferable, and among these, CH is specifically preferable.

In the formula (1), as X, NH, an oxygen atom or $CH_2NH$ is preferable, NH or an oxygen atom is more preferable, and NH is specifically preferable.

In the formula (1), as Y, an oxygen atom, a sulfur atom, NH, an N—$C_{1-6}$ alkyl or an N—$SO_2C_{1-6}$ alkyl is preferable, an oxygen atom or a sulfur atom is more preferable, and an oxygen atom is specifically preferable.

As $R^1$, $R^3$ and $R^4$, a hydrogen atom, a halogen atom and a $C_{1-6}$ alkyl group are preferable, and a hydrogen atom, a halogen atom or a $C_{1-4}$ alkyl group is specifically preferable. Among these, $R^1$ is more preferably a hydrogen atom or a halogen atom, and $R^3$ and $R^4$ are more preferably hydrogen atoms.

As $R^2$, a hydrogen atom, a —S(O)—$C_{1-6}$ alkyl, a —S(O)$_2$—$C_{1-6}$ alkyl and a 5-10 membered heteroaryl group optionally having substituents are preferable, a hydrogen atom, a —S(O)$_2$—$C_{1-4}$ alkyl and a 5-10 membered heteroaryl group optionally having substituents are more preferable, and a hydrogen atom, —$SO_2CH_3$ and a tetrazolyl group are specifically preferable.

As $R^5$, $R^6$, $R^7$ and $R^8$, a hydrogen atom is specifically preferable. As $R^9$, —C(O)$R^{19}$, —C(S)$R^{20}$, —S(O)$_2R^{21}$ and a 5-10 membered heteroaryl group optionally having substituents are preferable, and —C(O)R$^{19}$ and a 5-10 membered heteroaryl group optionally having substituents are specifically preferable. As R$^{19}$, a C$_{1-6}$ alkyl group, a C$_{1-6}$ alkoxy group, a halo C$_{1-5}$ alkoxy group, a halo C$_{3-8}$ cycloalkoxy group, a C$_{6-10}$ aryl C$_{1-6}$ alkoxy group, a phenyl group, a pyridyl group and a mono(C$_{1-6}$ alkyl)amino group are preferable. As R$^{20}$ and R$^{21}$, a C$_{1-6}$ alkyl group, a halo C$_{1-6}$ alkyl group, a C$_{3-8}$ cycloalkyl group, a mono(C$_{1-6}$ alkyl)amino group, a halo C$_{1-6}$ alkylphenyl group, C$_{1-6}$ alkoxyphenyl group and a thienyl group are preferable.

As the 5-10 membered heteroaryl group optionally having substituents, a pyridyl group or pyrimidinyl group optionally substituted by halogens, C$_{1-6}$ alkyls or halo C$_{1-6}$ alkyls is preferable.

As a more preferable compound of the condensed pyridine or condensed pyrimidine derivative represented by the formula (1), a compound selected from the group consisting of the following compounds may be exemplified:

tert-butyl 4-(4-{[2-fluoro-4-(methylsulfonyl)phenyl]amino}furo[3,2-d]pyrimidin-7-yl)piperidine-1-carboxylate (Example 1), 7-[1-(5-chloropyrimidin-2-yl)piperidin-4-yl]-N-[2-fluoro-4-(methylsulfonyl)phenyl]furo[3,2-d]pyrimidine-4-amine (Example 2), 7-[1-(5-ethylpyrimidin-2-yl)piperidin-4-yl]-N-[2-fluoro-4-(methylsulfonyl)phenyl]furo[3,2-d]pyrimidine-4-amine (Example 3), N-[2-fluoro-4-(methylsulfonyl)phenyl]-7-[1-(5-fluoropyrimidin-2-yl)piperidin-4-yl]furo[3,2-d]pyrimidine-4-amine (Example 4), 7-[1-(5-bromopyrimidin-2-yl)piperidin-4-yl]-N-[2-fluoro-4-(methylsulfonyl)phenyl]furo[3,2-d]pyrimidine-4-amine (Example 5), N-[2-fluoro-4-(methylsulfonyl)phenyl]-7-{1-[5-(trifluoromethyl)pyridin-2-yl]piperidin-4-yl}furo[3,2-d]pyrimidine-4-amine (Example 6), benzyl 4-(4-{[2-fluoro-4-(methylsulfonyl)phenyl]amino}furo[3,2-d]pyrimidin-7-yl)piperidine-1-carboxylate (Example 7), isopropyl 4-(4-{[2-fluoro-4-(methylsulfonyl)phenyl]amino}furo[3,2-d]pyrimidin-7-yl)piperidine-1-carboxylate (Example 8), ethyl 4-(4-{[2-fluoro-4-(methylsulfonyl)phenyl]amino}furo[3,2-d]pyrimidin-7-yl)piperidine-1-carboxylate (Example 9), 7-(1-{[3,5-bis(trifluoromethyl)phenyl]sulfonyl}piperidin-4-yl)-N-[2-fluoro-4-(methylsulfonyl)phenyl]furo[3,2-d]pyrimidine-4-amine (Example 10), 7-[1-(cyclopropylsulfonyl)piperidin-4-yl]-N-[2-fluoro-4-(methylsulfonyl)phenyl]furo[3,2-d]pyrimidine-4-amine (Example 11), 7-[1-(cyclohexylsulfonyl)piperidin-4-yl]-N-[2-fluoro-4-(methylsulfonyl)phenyl]furo[3,2-d]pyrimidine-4-amine (Example 12), N-[2-fluoro-4-(methylsulfonyl)phenyl]-7-[1-(thiophen-2-ylsulfonyl)piperidin-4-yl]furo[3,2-d]pyrimidine-4-amine (Example 13), N-[2-fluoro-4-(methylsulfonyl)phenyl]-7-{1-[(4-methoxyphenyl)sulfonyl]piperidin-4-yl}furo[3,2-d]pyrimidine-4-amine (Example 14), 7-[1-(butylsulfonyl)piperidin-4-yl]-N-[2-fluoro-4-(methylsulfonyl)phenyl]furo[3,2-d]pyrimidine-4-amine (Example 15), N-[2-fluoro-4-(methylsulfonyl)phenyl]-7-{1-[(trichloromethyl)sulfonyl]piperidin-4-yl}furo[3,2-d]pyrimidine-4-amine (Example 16), N-(tert-butyl)-4-(4-{[2-fluoro-4-(methylsulfonyl)phenyl]amino}furo[3,2-d]pyrimidin-7-yl)piperidine-1-carboxamide (Example 17), N-(tert-butyl)-4-(4-{[2-fluoro-4-(methylsulfonyl)phenyl]amino}furo[3,2-d]pyrimidin-7-yl)piperidine-1-carbothioamide (Example 18),

[4-(4-{[2-fluoro-4-(methylsulfonyl)phenyl]amino}furo[3,2-d]pyrimidin-7-yl)piperidin-1-yl](pyridin-2-yl)methanone (Example 19),

[4-(4-{[2-fluoro-4-(methylsulfonyl)phenyl]amino}furo[3,2-d]pyrimidin-7-yl) piperidin-1-yl](pyridin-3-yl)methanone (Example 20), tert-butyl 4-{4-[3-fluoro-4-(methylsulfonyl)phenoxy]furo[3,2-d]pyrimidin-7-yl}piperidine-1-carboxylate (Example 21), tert-butyl 4-{4-[(2-methylpyridin-3-yl)oxy]furo[3,2-d]pyrimidin-7-yl}piperidine-1-carboxylate (Example 22), tert-butyl 4-(4-{[4-(methylsulfonyl)benzyl]amino}furo[3,2-d]pyrimidin-7-yl)piperidine-1-carboxylate (Example 23), tert-butyl 4-{4-[5-(methylsulfonyl)indolin-1-yl]furo[3,2-d]pyrimidin-7-yl}piperidine-1-carboxylate (Example 24), 7-[1-(5-ethylpyrimidin-2-yl)piperidin-4-yl]-4-[5-(methylsulfonyl)indolin-1-yl]furo[3,2-d]pyrimidine (Example 25), 7-[1-(5-chloropyrimidin-2-yl)piperidin-4-yl]-4-[5-(methylsulfonyl)indolin-1-yl]furo[3,2-d]pyrimidine (Example 26), tert-butyl 4-(4-{[2-fluoro-4-(methylsulfonyl)phenyl]amino}thieno[3,2-d]pyrimidin-7-yl)piperidine-1-carboxylate (Example 27), tert-butyl 4-(4-{[2-fluoro-4-(methylsulfonyl)phenyl]amino}-5H-pyrrolo[3,2-d]pyrimidin-7-yl)piperidine-1-carboxylate (Example 28), tert-butyl 4-(4-{[2-fluoro-4-(methylsulfonyl)phenyl]amino}-5-(methanesulfonyl)-5H-pyrrolo[3,2-d]pyrimidin-7-yl)piperidine-1-carboxylate (Example 29), tert-butyl 4-(4-{[2-fluoro-4-(methylsulfonyl)phenyl]amino}-5-methyl-5H-pyrrolo[3,2-d]pyrimidin-7-yl)piperidine-1-carboxylate (Example 30)

N-[2-fluoro-4-(methylsulfonyl)phenyl]-7-{1-[5-(trifluoromethyl)pyrimidin-2-yl]piperidin-4-yl}furo[3,2-d]pyrimidine-4-amine (Example 31), 2,2,2-trifluoroethyl 4-(4-{[2-fluoro-4-(methylsulfonyl)phenyl]amino}furo[3,2-d]pyrimidin-7-yl)piperidine-1-carboxylate (Example 32), 1,1,1-trifluoro-2-methylpropan-2-yl 4-(4-{[2-fluoro-4-(methylsulfonyl)phenyl]amino}furo[3,2-d]pyrimidin-7-yl)piperidine-1-carboxylate (Example 33), 4,4-difluorocyclohexyl 4-(4-{[2-fluoro-4-(methylsulfonyl)phenyl]amino}furo[3,2-d]pyrimidin-7-yl)piperidine-1-carboxylate (Example 34), neopentyl 4-(4-{[2-fluoro-4-(methylsulfonyl)phenyl]amino}furo[3,2-d]pyrimidin-7-yl)piperidine-1-carboxylate (Example 35), 2,2,2-trichloroethyl 4-(4-{[2-fluoro-4-(methylsulfonyl)phenyl]amino}furo[3,2-d]pyrimidin-7-yl)piperidine-1-carboxylate (Example 36), phenyl 4-(4-{[2-fluoro-4-(methylsulfonyl)phenyl]amino}furo[3,2-d]pyrimidin-7-yl)piperidine-1-carboxylate (Example 37), 1-[4-(4-{[2-fluoro-4-(methylsulfonyl)phenyl]amino}furo[3,2-d]pyrimidin-7-yl)piperidin-1-yl]-3,3-dimethylbutan-1-one (Example 38), tert-butyl 4-(4-{[2-fluoro-4-(methylsulfonyl)phenyl](methyl)amino}furo[3,2-d]pyrimidin-7-yl)piperidine-1-carboxylate (Example 39), tert-butyl 4-(4-{4-(methylsulfonyl)phenoxy}furo[3,2-d]pyrimidin-7-yl)piperidine-1-carboxylate (Example 40), and tert-butyl 4-{4-[4-(1H-tetrazol-1-yl)phenoxy]furo[3,2-d]pyrimidin-7-yl}piperidine-1-carboxylate (Example 41).

In the case when a geometric isomer or an optical isomer of the compound of the present invention is present, those isomers are also encompassed within the scope of the present invention. These isomers are separated by conventional methods.

The salt of the compound represented by the formula (1) is not specifically limited as long as it is a pharmaceutically acceptable salt. In the case when the compound is handled as an acidic compound, salts of an alkali metal or an alkaline earth metal such as sodium, potassium, magnesium and calcium; salts of an organic base such as trimethylamine, triethylamine, pyridine, picoline, N-methylpyrrolidine, N-methylpiperidine, N-methylmorpholine and the like may be exemplified. In the case when the compound is handled as a basic compound, acid addition salts of mineral acids such as hydrochlorides, hydrobromides, hydroiodides, sulfates, nitrates and phosphates; acid addition salts of organic acids such as benzoates, methanesulfonates, ethanesulfonates, benzenesulfonates, p-toluenesulfonates, maleates, fumarates, tartrates, citrates and acetate, and the like may be exemplified.

Examples of the solvate of the compound represented by the formula (1) or a salt thereof may include, but are not limited to, hydrates and the like.

In addition, all of compounds that are metabolized in a living body and thereby converted into the compounds represented by the formula (1), so-called prodrugs, are also encompassed in the present invention. Examples of groups that form the prodrug of the compound of the present invention may include the groups described in "Progress in Medicine", Lifescience Medica, 1985, vol. 5, p. 2157-2161, and the groups described in "Iyakuhin no Kaihatsu (Development of Medicine)", vol. 7, Bunshi Sekkei (Molecular Design), p. 163-198, published in 1990 by Hirokawa Shoten.

The above-mentioned compound represented by the formula (1) or a salt thereof, or a solvate of the compound or the salt may be produced by various known methods but the methods are not specifically limited, and these compounds may be produced, for example, according to the reaction steps explained below. Furthermore, when the following reaction is conducted, the functional groups other than the reaction sites may be protected as necessary in advance and deprotected at a suitable stage. The conditions for protection and deprotection can be conducted referring to generally-used methods (for example, the methods described in Protective Groups inorganic Synthesis Third Edition, John Wiley & Sons, Inc., 1999). Furthermore, in each step, the reaction may be conducted by a generally-conducted method (for example, the method described in Comprehensive Organic Transformations Second Edition, John Wiley & Sons, Inc; 1999), and isolation and purification may be conducted by suitably selecting or combining general methods such as crystallization, recrystallization and chromatography.

(Method for Production of Compound Represented by Formula (1))

The compound represented by the formula (1) of the present invention can be produced by a method described in the following Reaction Scheme 1.

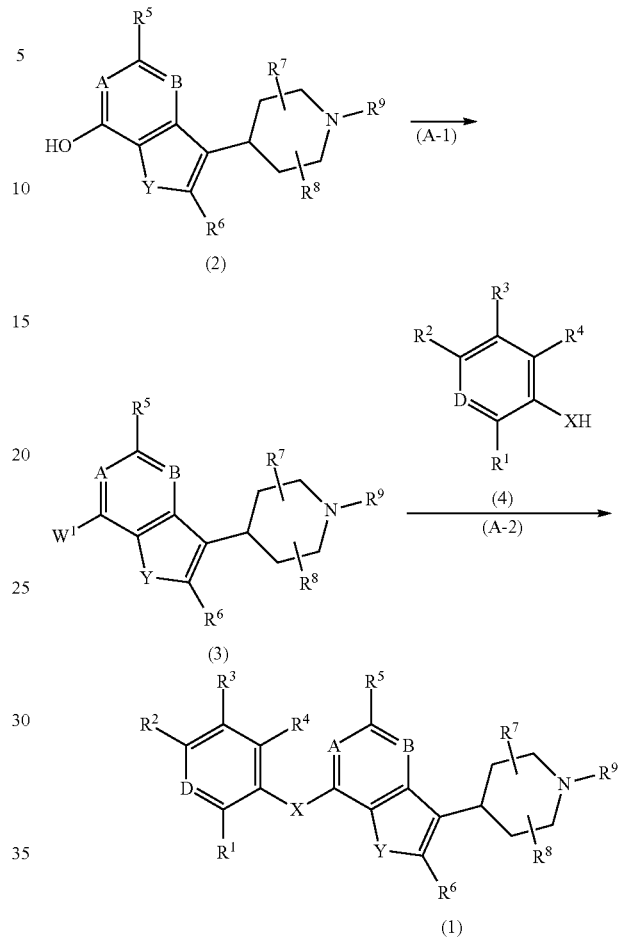

[Reaction Scheme 1]

wherein A, B, D, X, Y, $R^1$, $R^2$, $R^3$, $R^4$, $R^5$, $R^6$, $R^7$, $R^8$ and $R^9$ are as defined in the above-mentioned formula (1), and $W^1$ represents a leaving group.

(A-1) Step A-1 is a step in which Compound (3) is produced by reacting Compound (2) with a dehydration-condensation agent such as hexafluorophosphoric acid (benzotriazol-1-yloxy)tripyrrolidinophosphonium (PyBOP) or a sulfonylating agent such as methanesulfonyl chloride in a solvent in the presence of a base. The base as used is not specifically limited, and alkali metal carbonates such as lithium carbonate, sodium carbonate, potassium carbonate and cesium carbonate; organic bases such as 1,8-diazabicyclo[5.4.0]undec-7-ene (DBU), 1,5-diazabicyclo[4.3.0]non-5-ene (DBN), DABCO, triethylamine, N,N-diisopropylethylamine, N,N-diisopropylpentylamine and trimethylamine, and the like may be used. 1,8-Diazabicyclo[5.4.0]undec-7-ene (DBU) is preferable. The solvent as used is not specifically limited, and examples thereof are N,N-dimethylformamide, dioxane, tetrahydrofuran, acetonitrile, propionitrile, chloroform, methylene chloride and the like, and these may be used alone or in combination. Tetrahydrofuran alone or a mixed solvent of tetrahydrofuran and methylene chloride is preferable. The reaction temperature is 0 to 150° C., preferably 10 to 30° C. The reaction time is 5 minutes to 48 hours, preferably 10 minutes to 2 hours.

(A-2) Step A-2 is a step in which Compound (1) is produced by reacting Compound (3) with Compound (4) in a solvent in the presence of a base. The base as used is not specifically limited, and for example, alkali metal hydrides such as lithium hydride, sodium hydride and potassium hydride; alkali metals such as metallic lithium, metallic sodium and metallic potassium; alkali metal hydroxides such as lithium hydroxide, sodium hydroxide and potassium hydroxide; alkali metal carbonates such as lithium carbonate, sodium carbonate, potassium carbonate and cesium carbonate; lithium diisopropylamide, sodium diisopropylamide, potassium diisopropylamide, lithium hexamethyldisilazide, sodium hexamethyldisilazide, potassium hexamethyldisilazide, sodium tert-butoxide, potassium tert-butoxide, n-butyllithium, sec-butyllithium, tert-butyllithium, and the like may be used. Sodium hydride is preferable. The solvent as used is not specifically limited, and examples thereof are N,N-dimethylformamide, dioxane, tetrahydrofuran, acetonitrile, propionitrile and the like, and these may be used alone or in combination. N,N-dimethylformamide is preferable. The reaction temperature is 0 to 150° C., preferably 50 to 100° C. The reaction time is 10 minutes to 48 hours, preferably 30 minutes to 4 hours.

Besides the above-mentioned method, the compound represented by the formula (1) of the present invention may also be produced by a method described in the following Reaction Scheme 2.

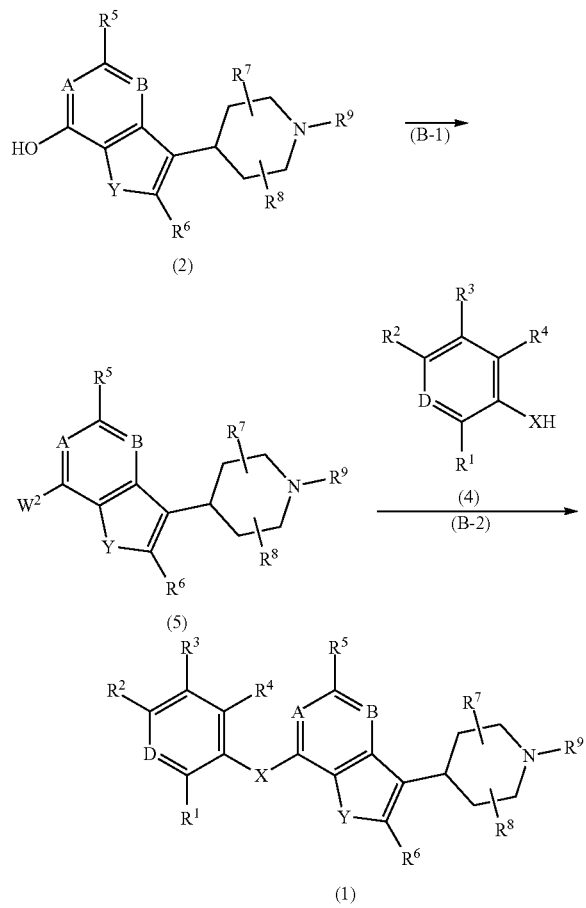

wherein A, B, D, X, Y, $R^1$, $R^2$, $R^3$, $R^4$, $R^5$, $R^6$, $R^7$, $R^8$ and $R^9$ are as defined in the above-mentioned formula (1), and $W^2$ represents a leaving group.

(B-1) Step B-1 is a step in which Compound (5) is produced by reacting Compound (2) with a halogenating agent such as phosphorus oxychloride ($POCl_3$) in the presence or absence of a solvent in the presence or absence of a base. The halogenating agent as used is not specifically limited, and phosphorus oxychloride, phosphorus oxychloride/phosphorus pentachloride, N,N-dimethylformamide/oxalyl chloride and the like may be used. Phosphorus oxychloride is preferable. As the base as used, N,N-dimethylaniline, N,N-diethylaniline, N,N,N-diisopropylethylamine and the like can be used. As the solvent as used, dioxane, 1,2-dichloroethane and the like may be used. The reaction temperature is 0 to 150° C., preferably 80 to 120° C. The reaction time is 10 minutes to 48 hours, preferably 3 to 6 hours.

(B-2) Step B-2 is a step in which the compound represented by the formula (1) is produced by reacting Compound (5) with Compound (4) through an amination reaction using a metal catalyst. Although the metal catalyst, ligand, base and reaction conditions as used are not specifically limited as long as they are reagents and conditions that are generally used in an amination reaction, for example, the method described in A. R. Muci, S. L. Buchwald, Top. Curr. Chem., 219, 131-209, (2002) or the like may be used. In Step B-2, a technique of an amination reaction conducted in a solvent or without a solvent in the presence or absence of a base in the presence of a metal catalyst may also be applied. In that technique, microwave irradiation may be conducted. The metal catalyst as used is not specifically limited, and a palladium complex such as palladium acetate (II), palladium (0) dibenzylideneacetone, tris(dibenzylideneacetone)dipalladium (0), bis(tri-tert-butylphosphine) palladium (0), tris(dibenzylideneacetone) (chloroform)dipalladium (0), [1,1'-bis(diphenylphosphino) ferrocene]dichloropalladium (II) and tetrakis(triphenylphosphine) palladium, or a monovalent copper reagent suchas cuprous iodide, cuprous bromide and cuprous cyanide may be used alone, or in combination with a ligand such as (2-biphenyl)di-tert-butylphosphine, (2-biphenyl)dicyclohexylphosphine, tricyclohexylphosphine, 1,3-bis(phenylphosphono) propane, 2,2'-bis(diphenylphosphanyl)-1,1'-binaphthyl, 2-(dicyclohexylphosphono)biphenyl, 2-dicyclohexylphosphino-2'-(N,N-dimethylamino)biphenyl, tetramethylethylenediamine, N,N'-dimethylethylenediamine, glycine, N,N-dimethylglycine and N-methylglycine. The base is not specifically limited, and alkali metal hydrides such as lithium hydride, sodium hydride and potassium hydride; alkali metals such as metallic lithium, metallic sodium and metallic potassium; alkali metal hydroxides such as lithium hydroxide, sodium hydroxide and potassium hydroxide; alkali metal carbonates such as lithium carbonate, sodium carbonate, potassium carbonate and cesium carbonate; lithium diisopropylamide, sodium diisopropylamide, potassium diisopropylamide, lithium hexamethyldisilazide, sodium hexamethyldisilazide, potassium hexamethyldisilazide, sodium tert-butoxide, potassium tert-butoxide, n-butyllithium, sec-butyllithium, tert-butyllithium, and the like may be used. Although the solvent is not specifically limited, for example, tetrahydrofuran, toluene, dioxane, N,N-dimethylformamide, N-methylpyrrolidone, dimethylsulfoxide, water and the like can be used alone or in combination. The reaction temperature is 0 to 200° C., preferably 100° C. to 150° C. The reaction time is 1 minute to 5 days, preferably 30 minutes to 6 hours.

(Method for Producing Piperidine Derivative Represented by Formula (2))

Next, Compound (2a) in which A and B are both nitrogen atoms in the compound represented by the formula (2) which is used in the above-mentioned reaction may be produced by a method described in the following Reaction Scheme 4.

[Reaction Scheme 3]

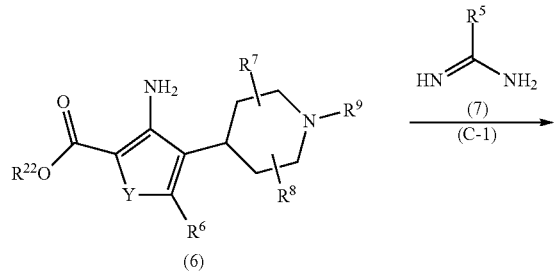

(C-1) Step C-1 is a step in which Compound (2) is produced by reacting Compound (6) with an amidine derivative (7) or a salt thereof. Although the solvent as used is not specifically limited, for example, methanol, ethanol, ether, tetrahydrofuran, 1,4-dioxane, benzene, toluene and the like may be used. Methanol is preferable. The reaction temperature is 40 to 120° C., preferably 80° C. to 100° C. The reaction time is 1 hour to 5 days, preferably 12 hours to 2 days. Furthermore, Compound (2) may also be produced by referring to WO2009/115496, JP 2008-222557 A, WO2002/057271. For Compound (7) used in the above-mentioned reaction, an available one may be used directly, or Compound (7) may be suitably produced by a known method, but is not limited thereto.

(Method for Producing Piperidine Derivative Represented by Formula (6))

The piperidine derivative represented by the formula (6) used in the above-mentioned reaction may be produced through a method described in the following Reaction Scheme 5.

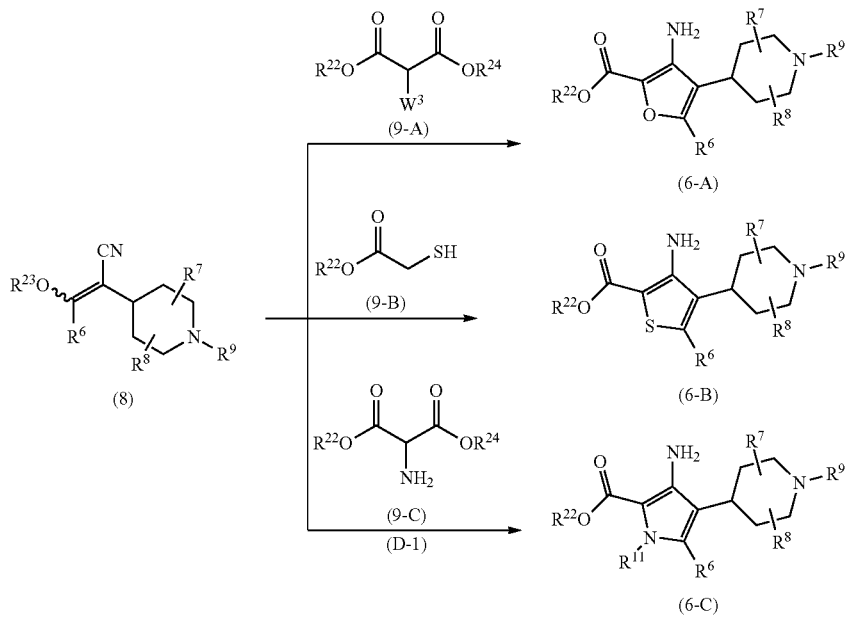

wherein $R^6$, $R^7$, $R^8$ and $R^9$ are as defined in the above-mentioned formula (1), $R^{23}$ represents a hydrogen atom or a metal ion, $R^{22}$ and $R^{24}$ each represent a $C_{1-6}$ alkyl group or a $C_{7-12}$ arylalkyl group, and $W^3$ represents a leaving group.

(D-1) Step D-1 is a step in which Compounds (6-A) to (6-C) are produced by reacting Compound (8) with a malonic acid derivative (9-A or C) or an acetic acid derivative (9-B). Compound (6-A) may be produced through referring to WO2009/115496, Compound (6-B) may be produced through referring to JP 2008-222557 A, and Compound (6-C) may be produced through referring to a known document such as J. Org. Chem., 1982, 47, 4633-4637.

The intermediates and objective substances obtained in the above-mentioned respective reactions may be isolated and purified as necessary by subjecting to a purification method that is conventionally used inorganic synthesis chemistry -continued

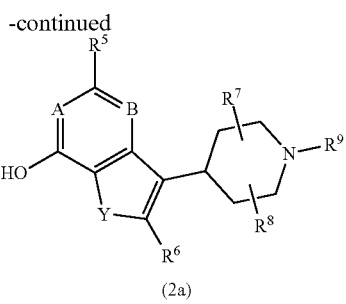

wherein A, B, Y, $R^5$, $R^6$, $R^7$, $R^8$ and $R^9$ are as defined in the above-mentioned formula (1), and $R^{22}$ represents a $C_{1-6}$ alkyl group or a $C_{7-12}$ arylalkyl group.

such as filtration, extraction, washing, drying, concentration, recrystallization, various chromatographies and the like. Alternatively, the intermediates may be subjected to the next reaction without undergoing specific purification.

Furthermore, various isomers may be isolated by applying a conventional method utilizing the difference between the physicochemical properties of the isomers. A racemic mixture can be brought to optically pure isomers by a general racemic resolution method, for example, a method including bringing to a diastereomer salt with a general optically active acid such as tartaric acid and followed by conducting optical resolution or a method using optically active column chromatography, or the like. Furthermore, the diastereomer mixture can be resolved by preparative crystallization or various chromatographies, or the like. In addition, an optically active compound may be produced by using a suitable optically active raw material.

Compound (1) as obtained may be formed into a salt by a general method. Furthermore, a solvate with a reaction solvent, a recrystallization solvent or the like, or a hydrate may also be formed.

Although a pharmaceutical containing the compound represented by the formula (1) or a salt thereof, or a solvate of the compound or the salt of the present invention as an active ingredient may use the active ingredient alone, the pharmaceutical is generally used by incorporating a pharmaceutically acceptable carrier, an additive and the like. The administration form of the pharmaceutical composition is not specifically limited and may be suitably selected according to the therapeutic purpose. For example, any of an oral agent, an injectable agent, a suppository, an ointment, an inhaler, an ophthalmic agent, a nasal agent and a patch may be used. Pharmaceutical compositions suitable for these administration forms may be produced through known formulation methods.

In the case when an oral solid preparation is prepared, tablets, coated tablet, a granules, powders, capsules or the like may be produced by adding an excipient, and a binder, a disintegrating agent, a lubricant, a colorant, a taste improving agent, an odor improving agent and the like as necessary, to the compound represented by the formula (1), and conducting a conventional method. The additive may be one that is generally used in the art. Examples of the excipient may include lactose, white sugar, sodium chloride, glucose, starch, calcium carbonate, kaolin, microcrystalline cellulose, silicic acid and the like. Examples of the binder may include water, ethanol, propanol, simple syrup, liquid glucose, liquid starch, liquid gelatin, carboxymethyl cellulose, hydroxypropyl cellulose, hydroxypropyl starch, methyl cellulose, ethyl cellulose, shellac, calcium phosphate, polyvinyl pyrrolidone and the like. Examples of the disintegrating agent may include dry starch, sodium alginate, agar powder, sodium hydrogencarbonate, calcium carbonate, sodium laurylsulfate, stearic acid monoglyceride, lactose and the like. Examples of the lubricant may include purified talc, stearates, borax, polyethylene glycol and the like. Examples of the taste improving agent may include white sugar, orange peel, citric acid, tartatic acid and the like.

In the case when an oral liquid preparation is prepared, an internal liquid, a syrup, an elixir agent and the like may be produced through a conventional method by adding a taste improving agent, a buffer, a stabilizer, an odor improving agent and the like to the compound represented by the formula (1). Examples of the taste improving agent may be those mentioned above, and examples of the buffer may include sodium citrate and the like, and examples of the stabilizer may include tragacanth, gum arabic, gelatin and the like.

In the case when an injectable agent is prepared, subcutaneous, intramuscular and intravenous injectable agents may be produced through a conventional method by adding a pH adjusting agent, a buffer, a stabilizer, an isotonic agent, a topical anesthetic and the like to the compound represented by the formula (1). Examples of the pH adjusting agent and buffer agent may include sodium citrate, sodium acetate, sodium phosphate and the like. Examples of the stabilizer may include sodium pyrophosphite, EDTA, thioglycolic acid, thiolactic acid and the like. Examples of the topical anesthetic may include procaine hydrochloride, lidocaine hydrochrolide and the like. Examples of the isotonic agent may include sodium chloride, glucose and the like.

In the case when a suppository is prepared, the suppository may be produced by adding to the compound represented by the formula (1) a known carrier for suppositories such as polyethylene glycol, lanolin, cocoa fat and an fatty acid triglyceride, and further adding a surfactant such as Tween (registered trademark) and the like as necessary, and thereafter conducting a conventional method.

In the case when an ointment is prepared, a base, a stabilizer, a wetting agent, a preservative and the like which are generally used are incorporated as necessary in the compound represented by the formula (1), and mixed and formulated by a conventional method. Examples of the base may include liquid paraffin, white vaseline, white beeswax, octyldodecyl alcohol, paraffin and the like. Examples of the preservative may include methyl p-hydroxybenzoate, ethyl p-hydroxybenzoate, propyl p-hydroxybenzoate and the like.

Besides the above-mentioned agents, the compound represented by the formula (1) may be formed into an inhaler, an eye drop and a nasal agent through conventional methods.

As indicated in Examples described below, the compound represented by the formula (1) has an action to significantly promote insulin secretion in hamster pancreatic β cell strain HIT-T15 cells. Therefore, the compound represented by the formula (1) or an acid addition salt thereof, or a solvate of the compound or the acid addition salt, is useful as a hypoglycemic agent, or as a prophylaxis and/or therapeutic agent for diseases caused by hyperglycemia such as diabetes mellitus in mammals including human. Specifically, diabetes mellitus may include non-insulin dependent diabetes mellitus (NIDDM).

The compound represented by the formula (1) of the present invention is administered by oral administration or parenteral administration. The dosage amount of the pharmaceutical of the present invention differs according to the body weight, age, sex, symptom and the like of a patient, and in the case of a general adult human, it is preferable to administer the compound represented by the formula (1) by 0.01 to 1,000 mg, preferably 0.1 to 300 mg per day in one to three portions.

EXAMPLES

Next, the present invention will further be explained referring to Examples, but the present invention is not limited to these Examples. The abbreviations used in the following Examples have the following means.

s: singlet
d: doublet
t: triplet
q: quartet
quint: quintet
m: multiplet
br: broad
J: coupling constant
Hz: Hertz CDCl$_3$: deuterated chloroform
d$_6$-DMSO: deuterated dimethylsulfoxide
CD$_3$OD: deuterated methanol
$^1$H-NMR: proton nuclear magnetic resonance
IR: infrared ray absorption spectrum Example 1

Production of Tert-Butyl 4-(4-{[2-fluoro-4-(methylsulfonyl)phenyl]amino}furo[3,2-d]pyrimidin-7-yl)piperidine-1-carboxylate Step 1: production of tert-butyl 4-hydroxymethylpiperidine-1-carboxylate 4-Piperidinemethanol (4.6 g, 40 mmol) was dissolved in tetrahydrofuran (40 mL) and water (40 mL), di-tert-butyl dicarbonate (9.6 g, 44 mmol) and carbonate sodium (5.1 g, 48 mmol) were added, and stirring was conducted at room temperature overnight. Water was added to the reaction liquid, and extraction was conducted by using ethyl acetate. The organic layer was dried over anhydrous sodium sulfate and concentrated under a reduced pressure to give tert-butyl 4-hydroxymethylpiperidine-1-carboxylate (12.9 g) as a crude purified product.

Step 2: Production of tert-butyl 4-{[(methylsulfonyl)oxy]methyl}piperidine-1-carboxylate Under an argon atmosphere, the tert-butyl-4-hydroxymethylpiperidine-1-carboxylate obtained in Step 1 (12.9 g, crude) was dissolved in anhydrous tetrahydrofuran (100 mL), triethylamine (17 mL, 120 mmol) was added, thereafter methanesulfonyl chloride (3.5 mL, 44 mmol) was added dropwise under ice-cooling over about 10 minutes, and stirring was further conducted under ice-cooling for 30 minutes. Water was added to the reaction liquid to quench the reaction, and the reaction liquid was extracted with ethyl acetate. The organic layer was dried over anhydrous sodium sulfate and concentrated under a reduced pressure to give tert-butyl-4-{[(methylsulfonyl)oxy]methyl}piperidine-1-carboxylate (15.3 g) as a crude purified product.

Step 3: Production of tert-butyl 4-(cyanomethyl)piperidine-1-carboxylate tert-Butyl 4-{[(methylsulfonyl)oxy]methyl}piperidine-1-carboxylate (15.3 g) was dissolved in ethanol (80 mL), water (20 mL) and sodium cyanide (4.0 g, 80 mmol) were added, and stirring was conducted at 80° C. for 24 hours. Ethanol was distilled off, water and ethyl acetate were added, and then the resultant mixture was subject to Celite filtration, followed by extraction with ethyl acetate. The organic layer was washed with saturated brine, dried over anhydrous sodium sulfate and concentrated under a reduced pressure, and the obtained residue was purified by using silica gel column chromatography (hexane:ethyl acetate=3:1→2:1) to give tert-butyl 4-(cyanomethyl)piperidine-1-carboxylate (6.87 g, 77%, 3 steps) as a white solid.
$^1$H-NMR (CDCl$_3$) δ: 1.21-1.31 (2H, m), 1.46 (9H, s), 1.78-1.86 (3H, m), 2.31 (2H, d, J=6.4 Hz), 2.64-2.78 (2H, m), 4.07-4.21 (2H, m).

Step 4: Production of tert-butyl 4-(1-cyano-2-oxoethyl)piperidine-1-carboxylate

Under an argon atmosphere, tert-butyl 4-(cyanomethyl)piperidine-1-carboxylate (2.24 g, 10 mmol) and potassium tert-butoxide (6.73 g, 60 mmol) were dissolved in anhydrous N,N-dimethyl formamide (15 mL), and a solution of ethyl formate (4.44 g, 60 mmol) in anhydrous N,N-dimethylformamide (10 mL) was added dropwise under ice-cooling. The temperature was gradually raised to room temperature, and then the resultant mixture was stirred overnight. Water was added to the reaction liquid, followed by extraction with ethyl acetate. 1 N hydrochloric acid was added to the obtained aqueous layer until it reached a pH of 6, and then the resultant mixture was extracted with ethyl acetate. The organic layer was dried over anhydrous sodium sulfate and concentrated under a reduced pressure to give tert-butyl 4-(1-cyano-2-oxoethyl)piperidine-1-carboxylate (2.35 g) as a crude product.

Step 5: Production of tert-butyl 4-[4-amino-5-(ethoxycarbonyl)furan-3-yl]piperazine-1-carboxylate tert-Butyl 4-(1-cyano-2-oxoethyl)piperidine-1-carboxylate (2.35 g, crude product), diethyl chloromalonate (1.94 g, 10 mmol) and 1,8-diazabicyclo[5.4.0]undec-7-ene (4.56 g, 30 mmol) were dissolved in tetrahydrofuran (20 mL), followed by stirring at room temperature overnight. Water was added to the reaction liquid, followed by extraction with ethyl acetate, and the organic layer was dried over anhydrous sodium sulfate and concentrated under a reduced pressure. The obtained residue was purified by using silica gel column chromatography (hexane:ethyl acetate=6:1→2:1) to give tert-butyl 4-[4-amino-5-(ethoxycarbonyl) furan-3-yl]piperazine-1-carboxylate (1.30 g, 38%, 2 steps) as a yellow solid.
$^1$H-NMR (CDCl$_3$) δ: 1.38 (3H, t, J=7.1 Hz), 1.47 (9H, s), 1.87-1.95 (2H, m), 2.38-2.49 (1H, m), 2.74-2.87 (2H, m), 4.10-4.28 (2H, m), 4.35 (2H, q, J=7.1 Hz), 4.50 (2H, brs), 7.06 (1H, s).

Step 6: Production of tert-butyl 4-(4-hydroxyfuro[3,2-d]pyrimidin-7-yl)piperidine-1-carboxylate tert-Butyl 4-[4-amino-5-(ethoxycarbonyl)furan-3-yl]piperazine-1-carboxylate (1.30 g, 3.84 mmol) and formamidine acetate (2.00 g, 19.2 mmol) were dissolved in ethanol (20 mL), and the resultant solution was heated to reflux for 2 days. The ethanol was distilled off, water and diethyl ether were then added to the obtained residue, and the precipitated solid was separated by filtration and washed with diethyl ether and hexane to give tert-butyl 4-(4-hydroxyfuro[3,2-d]pyrimidin-7-yl)piperidine-1-carboxylate (825 mg, 68%) as a brown solid.
$^1$H-NMR (CDCl$_3$) δ: 1.48 (9H, s), 1.61-1.71 (2H, m), 2.03-2.12 (2H, m), 2.80-3.00 (3H, m), 4.08-4.35 (2H, m), 7.61 (1H, d, J=1.0 Hz), 8.04 (1H, s).

Step 7: Production of tert-butyl 4-{4-[(1H-benzo[d][1,2,3]triazol-1-yl)oxy]furo[3,2-d]pyrimidin-7-yl}piperidine-1-carboxylate Under an argon atmosphere, tert-butyl 4-(4-hydroxyfuro[3,2-d]pyrimidin-7-yl)piperidine-1-carboxylate (1.06 g, 3.22 mmol) and 1H-benzotriazol-1-yloxytripyrrolidinophosphonium hexafluorophosphate (1.81 g, 3.49 mmol) were dissolved in anhydrous tetrahydrofuran (17 mL), 1,8-diazabicyclo[5.4.0]undec-7-ene (656 mg, 4.31 mmol) was added to the solution, and then the resultant solution was stirred at room temperature for 40 minutes. Water was added to the reaction liquid, and the reaction liquid was extracted with ethyl acetate, dried over anhydrous sodium sulfate and concentrated under a reduced pressure, and the obtained residue was purified by silica gel column chromatography (hexane:ethyl acetate=2:1) to give tert-butyl 4-{4-[(1H-benzo[d][1,2,3]triazol-1-yl)oxy]furo[3,2-d]pyrimidin-7-yl}piperidine-1-carboxylate (1.19 g, 83%) as a white amorphous.

$^1$H-NMR (CDCl$_3$) δ: 1.48 (9H, s), 1.72 (2H, ddd, J=4.0, 12.6, 25.0 Hz), 2.12-2.18 (2H, m), 2.84-2.98 (2H, m), 3.08 (1H, dddd, J=3.4, 3.6, 11.6, 11.8 Hz), 4.16-4.34 (2H, m), 7.45-7.52 (2H, m), 7.55-7.59 (1H, m), 7.80 (1H, d, J=1.0 Hz), 8.15 (1H, d, J=8.3 Hz), 8.53 (1H, s).

Step 8: Production of tert-butyl 4-(4-{[2-fluoro-4-(methylsulfonyl)phenyl]amino}furo[3,2-d]pyrimidin-7-yl)piperidine-1-carboxylate Under an argon atmosphere, tert-butyl 4-{4-[(1H-benzo[d][1,2,3]triazol-1-yl)oxy]furo[3,2-d]pyrimidin-7-yl}piperidine-1-carboxylate (1.06 g, 2.44 mmol) and 2-fluoro-4-(methylsulfonyl)aniline (370 mg, 1.95 mmol) were dissolved in anhydrous N,N-dimethyl formaldehyde (13 mL), sodium hydride (130 mg, 2.68 mmol) was added slowly under ice-cooling, followed by stirring at 70° C. for 3 hours. Ethyl acetate was added, the insoluble matter was separated by filtration, water was added, followed by extraction with ethyl acetate. The organic layer was dried over anhydrous sodium sulfate and concentrated under a reduced pressure, and the obtained residue was purified by using silica gel column chromatography (chloroform:acetone=40:1→20:1→10:1) to give the titled compound (536 mg, 560) as a brown solid.

Example 2

Production of 7-[1-(5-chloropyrimidin-2-yl)piperidin-4-yl]-N-[2-fluoro-4-(methylsulfonyl)phenyl]furo[3,2-d]pyrimidine-4-amine Step 1: Production of N-[2-fluoro-4-(methylsulfonyl)phenyl]-7-(piperidin-4-yl)furo[3,2-d]pyrimidine-4-amine hydrochloride tert-butyl 4-(4-{[2-fluoro-4-(methylsulfonyl)phenyl]amino}furo[3,2-d]pyrimidin-7-yl)piperidine-1-carboxylate was suspended in ethyl acetate (3 mL), 4 N hydrochloric acid/ethyl acetate (3 mL) was added slowly under ice-cooling, followed by stirring at room temperature for 1 hour. After separation by filtration, washing was conducted by using ethyl acetate and diethyl ether to give N-[2-fluoro-4-(methylsulfonyl)phenyl]-7-(piperidin-4-yl)furo[3,2-d]pyrimidine-4-amine hydrochloride (267 mg) as a brown solid.

$^1$H-NMR (CD$_3$OD) δ: 1.98-2.08 (2H, m), 2.32-2.39 (2H, m), 3.11-3.27 (6H, m), 3.50-3.59 (2H, m), 7.83-7.92 (2H, m), 8.19 (1H, t, J=10.0 Hz), 8.26 (1H, s), 8.72 (1H, s).

Step 2: Production of 7-[1-(5-chloropyrimidin-2-yl)piperidin-4-yl]-N-[2-fluoro-4-(methylsulfonyl)phenyl]furo[3,2-d]pyrimidine-4-amine N-[2-fluoro-4-(methylsulfonyl)phenyl]-7-(piperidin-4-yl)furo[3,2-d]pyrimidine-4-amine hydrochloride (9.8 mg, 0.023 mmol), 2,5-dichloropyrimidine (5.1 mg, 0.035 mmol) and N,N-diisopropylethylamine (9.0 mg, 0.069 mmol) were dissolved in N,N-dimethylformamide (0.5 mL) and stirred at 80° C. for 2.5 hours. Water was added to the reaction liquid, and the reaction liquid was extracted with ethyl acetate, dried over anhydrous sodium sulfate and concentrated under a reduced pressure, and the obtained residue was purified by silica gel preparative thin layer chromatography (chloroform:methanol=25:1) to give the titled compound (2.2 mg, 19%) as a yellow solid.

Example 3

Production of 7-[1-(5-ethylpyrimidin-2-yl)piperidin-4-yl]-N-[2-fluoro-4-(methylsulfonyl)phenyl]furo[3,2-d]pyrimidine-4-amine The titled compound was obtained as a pale yellow solid by reacting and treating in the same manner as in Step 2 of Example 2 by using 2-chloro-5-ethylpyrimidine instead of 2,5-dichloropyrimidine.

Example 4

Production of N-[2-fluoro-4-(methylsulfonyl)phenyl]-7-[1-(5-fluoropyrimidin-2-yl)piperidin-4-yl]furo[3,2-d]pyrimidine-4-amine The titled compound was obtained as a pale yellow solid by reacting and treating in the same manner as in Step 2 of Example 2 by using 2-chloro-5-fluoropyrimidine instead of 2,5-dichloropyrimidine.

Example 5

Production of 7-[1-(5-bromopyrimidin-2-yl)piperidin-4-yl]-N-[2-fluoro-4-(methylsulfonyl)phenyl]furo[3,2-d]pyrimidine-4-amine The titled compound was obtained as a pale yellow solid by reacting and treating in the same manner as in Step 2 of Example 2 by using 2-chloro-5-bromopyrimidine instead of 2,5-dichloropyrimidine.

Example 6

Production of N-[2-fluoro-4-(methylsulfonyl)phenyl]-7-{1-[5-(trifluoromethyl)pyridin-2-yl]piperidin-4-yl}furo[3,2-d]pyrimidine-4-amine The titled compound was obtained as a pale yellow solid by reacting and treating in the same manner as in Step 2 of Example 2 by using 2-chloro-5-trifluoromethylpyridine instead of 2,5-dichloropyrimidine.

Example 7

Production of benzyl 4-(4-{[2-fluoro-4-(methylsulfonyl)phenyl]amino}furo[3,2-d]pyrimidin-7-yl)piperidine-1-carboxylate N-[2-Fluoro-4-(methylsulfonyl)phenyl]-7-(piperidin-4-yl)furo[3,2-d]pyrimidine-4-amine hydrochloride (9.0 mg, 0.021 mmol) was dissolved in pyridine (0.4 mL), and a 0.25 mol/L solution of benzyl chloroformate in anhydrous methylene chloride (0.1 mL) was added dropwise slowly under ice-cooling, and then the resultant mixture was stirred for 15 minutes under ice-cooling, and water was added, followed by extraction with ethyl acetate. The organic layer was dried over anhydrous sodium sulfate and concentrated under a reduced pressure, and the obtained residue was purified by silica gel preparative thin layer chromatography (chloroform:methanol=20:1) to give the titled compound (5.6 mg, 51%) as a yellow oily substance.

Example 8

Production of isopropyl 4-(4-{[2-fluoro-4-(methylsulfonyl)phenyl]amino}furo[3,2-d]pyrimidin-7-yl)piperidine-1-carboxylate The titled compound was obtained as a pale yellow solid by reacting and treating in similar manners to those in Example 7 by using isopropyl chloroformate instead of benzyl chloroformate.

Example 9

Production of ethyl 4-(4-{[2-fluoro-4-(methylsulfonyl)phenyl]amino}furo[3,2-d]pyrimidin-7-yl)piperidine-1-carboxylate The titled compound was obtained as a pale yellow solid by reacting and treating in the same manner as in Example 7 by using ethyl chloroformate instead of benzyl chloroformate.

Example 10

Production of 7-(1-{[3,5-bis(trifluoromethyl)phenyl]sulfonyl}piperidin-4-yl)-N-[2-fluoro-4-(methylsulfonyl)phenyl]furo[3,2-d]pyrimidine-4-amine N-[2-Fluoro-4-(methylsulfonyl)phenyl]-7-(piperidin-4-yl)furo[3,2-d]pyrimidine-4-amine hydrochloride (10 mg, 0.023 mmol) was dissolved in pyridine (0.1 mL), a solution of 3,5-bis(trifluoromethyl)benzene-1-sulfonyl chloride (14 mg, 0.046 mmol) in anhydrous methylene chloride (0.4 mL) was added under ice-cooling, followed by stirring at room temperature for 1 hour and 45 minutes. Water was added to the reaction liquid, followed by extraction with ethyl acetate, the organic layer was dried over anhydrous sodium sulfate and concentrated under a reduced pressure, and the obtained residue was purified by silica gel preparative thin layer chromatography (chloroform:methanol=50:1) to give the titled compound (6.3 mg, 41%) as a white solid.

Example 11

Production of 7-[1-(cyclopropylsulfonyl)piperidin-4-yl]-N-[2-fluoro-4-(methylsulfonyl)phenyl]furo[3,2-d]pyrimidine-4-amine A solution of cyclopropanesulfonyl chloride (4 mg, 0.028 mmol) in anhydrous acetonitrile (0.2 mL), and triethylamine (10 μL, 0.069 mmol) were added to N-[2-fluoro-4-(methylsulfonyl)phenyl]-7-(piperidin-4-yl)furo[3,2-d]pyrimidine-4-amine hydrochloride (10 mg, 0.023 mmol) under ice-cooling, followed by stirring at room temperature for 2 hours. Water was added to the reaction liquid, followed by extraction with chloroform, and the organic layer was dried over anhydrous sodium sulfate and concentrated under a reduced pressure, and the obtained residue was purified by silica gel preparative thin layer chromatography (chloroform:methanol=50:1) to give the titled compound (8.5 mg, 75%) as a pale yellow solid.

Example 12

Production of 7-[1-(cyclohexylsulfonyl)piperidin-4-yl]-N-[2-fluoro-4-(methylsulfonyl)phenyl]furo[3,2-d]pyrimidine-4-amine The titled compound was obtained as a pale yellow solid by reacting and treating in the same manner as in Example 11 by using cyclohexanesulfonyl chloride instead of cyclopropanesulfonyl chloride.

Example 13

Production of N-[2-fluoro-4-(methylsulfonyl)phenyl]-7-[1-(thiophen-2-ylsulfonyl)piperidin-4-yl]furo[3,2-d]pyrimidine-4-amine The titled compound was obtained as a pale yellow solid by reacting and treating in the same manner as in Example 11 by using thiophen-2-sulfonyl chloride instead of cyclopropanesulfonyl chloride.

Example 14

Production of N-[2-fluoro-4-(methylsulfonyl)phenyl]-7-{1-[(4-methoxyphenyl)sulfonyl]piperidin-4-yl}furo[3,2-d]pyrimidine-4-amine The titled compound was obtained as a pale yellow solid by reacting and treating in the same manner as in Example 11 by using 4-methoxybenzenesulfonyl chloride instead of cyclopropanesulfonyl chloride.

Example 15

Production of 7-[1-(butylsulfonyl)piperidin-4-yl]-N-[2-fluoro-4-(methylsulfonyl)phenyl]furo[3,2-d]pyrimidine-4-amine The titled compound was obtained as a pale yellow solid by reacting and treating in the same manner as in Example 11 by using butanesulfonyl chloride instead of cyclopropanesulfonyl chloride.

Example 16

Production of N-[2-fluoro-4-(methylsulfonyl)phenyl]-7-{1-[(trichloromethyl)sulfonyl]piperidin-4-yl}furo[3,2-d]pyrimidine-4-amine The titled compound was obtained as a pale yellow solid by reacting and treating in similar manners to those in Example 11 by using trichloromethanesulfonyl chloride instead of cyclopropanesulfonyl chloride.

Example 17

Production of N-(tert-butyl)-4-(4-{[2-fluoro-4-(methylsulfonyl)phenyl]amino}furo[3,2-d]pyrimidine-7-yl)piperidine-1-carboxamide A solution of 2-isocyanate-2-methylpropane (2.7 mg, 0.028 mmol) in anhydrous tetrahydrofuran (0.2 mL), and triethylamine (10 μL, 0.069 mmol) were added to N-[2- fluoro-4-(methylsulfonyl)phenyl]-7-(piperidin-4-yl)furo[3,2-d]pyrimidine-4-amine hydrochloride (10 mg, 0.023 mmol) under ice-cooling, and stirring was conducted at room temperature for 1 hour. Water was added to the reaction liquid, the reaction liquid was extracted with chloroform, the organic layer was dried over anhydrous sodium sulfate and concentrated under a reduced pressure, and the obtained residue was purified by silica gel preparative thin layer chromatography (chloroform:methanol=50:1) to give the titled compound (5.5 mg, 49%) as a pale yellow solid.

Example 18

Production of N-(tert-butyl)-4-(4-{[2-fluoro-4-(methylsulfonyl)phenyl]amino}furo[3,2-d]pyrimidine-7-yl)piperidine-1-carbothioamide The titled compound was obtained as a pale yellow solid by reacting and treating in the same manner as in Example 17 by using 2-isothiocyanate-2-methylpropane instead of 2-isocyanate-2-methylpropane.

Example 19

Production of [4-(4-{[2-fluoro-4-(methylsulfonyl)phenyl]amino}furo[3,2-d]pyrimidin-7-yl)piperidin-1-yl](pyridin-2-yl)methanone Under an argon atmosphere, anhydrous methylene chloride (0.5 mL) and triethylamine (10 μL, 0.069 mmol) were added to N-[2-fluoro-4-(methylsulfonyl)phenyl]-7-(piperidin-4-yl)furo[3,2-d]pyrimidine-4-amine hydrochloride (10 mg, 0.023 mmol), picolinic acid (3.3 mg, 0.028 mmol), 1-ethyl-3-(3-dimethylaminopropyl)carbodiimide hydrochloride (9 mg, 0.046 mmol) and N,N-dimethylaminopyridine (0.3 mg, 0.002 mmol), followed by stirring at room temperature for 2 hours. Water was added to the reaction liquid, the reaction liquid was extracted with chloroform, the organic layer was dried over anhydrous sodium sulfate and concentrated under a reduced pressure, and the obtained residue was purified by silica gel preparative thin layer chromatography (chloroform:methanol=20:1) to give the titled compound (3.3 mg, 35%) as a yellow oily substance.

Example 20

Production of [4-(4-{[2-fluoro-4-(methylsulfonyl)phenyl]amino}furo[3,2-d]pyrimidin-7-yl)piperidin-1-yl](pyridin-3-yl)methanone The titled compound was obtained as a pale yellow solid by reacting and treating in the same manner as in Example 19 by using nicotinic acid instead of picolinic acid.

Example 21

Production of tert-butyl 4-{4-[3-fluoro-4-(methylsulfonyl)phenoxy]furo[3,2,d]pyrimidin-7-yl}piperidine-1-carboxylate The titled compound was obtained as a pale yellow solid by reacting and treating in the same manner as in Step 8 of Example 1 by using 3-fluoro-4-(methylsulfonyl)phenol instead of 2-fluoro-4-(methylsulfonyl)aniline.

Example 22

Production of tert-butyl 4-{4-[(2-methylpyridin-3-yl)oxy]furo[3,2-d]pyrimidin-7-yl}piperidine-1-carboxylate The titled compound was obtained as a pale yellow solid by reacting and treating in the same manner as in Step 8 of Example 1 by using 3-hydroxy-2-methylpyridine instead of 2-fluoro-4-(methylsulfonyl)aniline.

Example 23

Production of tert-butyl 4-(4-{[4-(methylsulfonyl)benzyl]amino}furo[3,2-d]pyrimidin-7-yl)piperidine-1-carboxylate The titled compound was obtained as a pale yellow solid by reacting and treating in the same manner as in Step 8 of Example 1 by using [4-(methylsulfonyl)phenyl]methaneamine instead of 2-fluoro-4-(methylsulfonyl)aniline.

Example 24

Production of tert-butyl 4-{4-[5-(methylsulfonyl)indolin-1-yl]furo[3,2-d]pyrimidin-7-yl}piperidine-1-carboxylate The titled compound was obtained as a pale yellow solid by reacting and treating in the same manner as in Step 8 of Example 1 by using 5-(methylsulfonyl)indoline instead of 2-fluoro-4-(methylsulfonyl)aniline.

Example 25

Production of 7-[1-(5-ethylpyrimidin-2-yl)piperidin-4-yl]-4-[5-(methylsulfonyl)indolin-1-yl]furo[3,2-d]pyrimidine Step 1: Production of 4-[5-(methylsulfonyl)indolin-1-yl]-7-(piperidin-4-yl)furo[3,2-d]pyrimidine hydrochloride 4-[5-(Methylsulfonyl)indolin-1-yl]-7-(piperidin-4-yl)furo[3,2-d]pyrimidine hydrochloride was obtained as a pale yellow solid by reacting and treating in similar manners to those in Step 1 of Example 2 by using tert-butyl 4-{4-[5-(methylsulfonyl)indolin-1-yl]furo[3,2-d]pyrimidin-7-yl}piperidine-1-carboxylate instead of tert-butyl 4-(4-{[2-fluoro-4-(methylsulfonyl)phenyl]amino}furo[3,2-d]pyrimidin-7-yl)piperidine-1-carboxylate.

$^1$H-NMR (CD$_3$OD) δ: 1.95-2.08 (2H, m), 2.31-2.40 (2H, m), 3.13 (3H, s), 3.22-3.34 (3H, m), 3.51-3.59 (4H, m), 4.93 (2H, t, J=8.3 Hz), 7.90 (1H, d, J=8.3 Hz), 7.94 (1H, s), 8.48 (1H, s), 8.88 (1H, d, J=8.8 Hz), 8.96 (1H, s)

Step 2: Production of 7-[1-(5-ethylpyrimidin-2-yl)piperidin-4-yl]-4-[5-(methylsulfonyl)indolin-1-yl]furo[3,2-d]pyrimidine The titled compound was obtained as a pale yellow solid by reacting and treating in the same manner as in Step 2 of Example 2 by using 4-[5-(methylsulfonyl)indolin-1-yl]-7-(piperidin-4-yl)furo[3,2-d]pyrimidine hydrochloride instead of N-[2-fluoro-4-(methylsulfonyl)phenyl]-7-(piperidin-4-yl)furo[3,2-d]pyrimidine-4-amine hydrochloride, and using 2-chloro-5-ethylpyrimidine instead of 2,5-dichloropyrimidine.

Example 26

Production of 7-[1-(5-chloropyrimidin-2-yl)piperidin-4-yl]-4-[5-(methylsulfonyl)indolin-1-yl]furo[3,2-d]pyrimidine The titled compound was obtained as a pale yellow solid by reacting and treating in the same manner as in Step 2 of Example 2 by using 4-[5-(methylsulfonyl)indolin-1-yl]-7-(piperidin-4-yl)furo[3,2-d]pyrimidine hydrochloride instead of N-[2-fluoro-4-(methylsulfonyl)phenyl]-7-(piperidin-4-yl)furo[3,2-d]pyrimidine-4-amine hydrochloride.

Example 27

Production of tert-butyl 4-(4-{[2-fluoro-4-(methylsulfonyl)phenyl]amino}thieno[3,2-d]pyrimidin-7-yl)piperidine-1-carboxylate Step 1: Production of tert-butyl 4-[4-amino-5-(ethoxycarbonyl)thiophen-3-yl]piperidine-1-carboxylate The tert-butyl 4-(1-cyano-2-oxoethyl)piperidine-1-carboxylate (926 mg, 3.68 mmol) obtained in Step 4 of Example 1 was dissolved in dichloromethane (8 mL), a solution of triethylamine (0.66 mL, 4.78 mmol) and methanesulfonyl chloride (0.31 mL, 4.05 mmol) in dichloromethane (2 mL) was added dropwise under ice-cooling, followed by stirring under ice-cooling for 1 hour. The reaction liquid was diluted with chloroform, and the organic layer was washed with saturated brine, dried over anhydrous sodium sulfate and concentrated under a reduced pressure. The obtained residue (1.58 g) was dissolved in dichloromethane (20 mL), 1,8-diazabicyclo[4,3,0]-7-undecene (2.13 mL, 17.2 mmol) and 2-mercaptoethyl acetate (0.31 mL, 4.05 mmol) were added under ice-cooling, followed by stirring under ice-cooling for 3 hours. The reaction liquid was diluted with chloroform, and washed with a 1 N aqueous hydrochloric acid solution. The organic layer was washed with saturated brine, dried over anhydrous sodium sulfate and concentrated under a reduced pressure. The obtained residue (3.26 g) was dissolved in ethanol (20 mL), and then sodium ethoxide (2.0 g, 29.4 mmol) was added, followed by heating under reflux for 3 hours. The reaction liquid was concentrated under a reduced pressure, and the obtained residue was dissolved in chloroform. The organic layer was washed with saturated brine, dried over anhydrous sodium sulfate and concentrated under a reduced pressure. The obtained residue was purified by using silica gel chromatography (chloroform:methanol=50:1→30:1) to give tert-butyl 4-[4-amino-5-(ethoxycarbonyl)thiophen-3-yl]piperidine-1-carboxylate (287 mg, 22.0%) as a pale yellow amorphous.
$^1$H-NMR (CDCl$_3$) δ: 1.35 (3H, t, J=7.1 Hz), 1.47 (9H, s), 1.52-1.69 (2H, m), 1.90 (2H, d, J=13.4 Hz), 2.45 (1H, tt, J=3.5, 12.0 Hz), 2.74-2.88 (2H, m), 4.25-4.36 (4H, m), 5.45 (2H, brs), 6.96 (1H, s).

Step 2: Production of tert-butyl 4-(4-oxo-3,4-dihydrothieno[3,2-d]pyrimidin-7-yl)piperidine-1-carboxylate tert-Butyl 4-[4-amino-5-(ethoxycarbonyl)thiophen-3-yl]piperidine-1-carboxylate (307 mg, 0.87 mmol) was dissolved in ethanol (8 mL), and then formamidine acetate (542 mg, 5.20 mmol) was added, followed by heating under reflux for 36 hours. The reaction liquid was concentrated under a reduced pressure, and the obtained residue was dissolved in chloroform. The organic layer was washed with saturated brine, dried over anhydrous sodium sulfate and concentrated under a reduced pressure. The obtained residue was purified by using silica gel chromatography (chloroform:methanol=10:1) to give tert-butyl 4-(4-oxo-3,4-dihydrothieno[3,2-d]pyrimidin-7-yl)piperidine-1-carboxylate (62.5 mg, 21.5%) as a pale yellow amorphous.
$^1$H-NMR (CDCl$_3$) δ: 1.49 (9H, s), 1.56-1.70 2H, m), 2.04 (2H, d, J=12.4 Hz), 2.81-2.99 (2H, m), 3.15-3.26 (1H, m), 4.25 (2H, brs), 7.50 (1H, s), 8.16 (1H, s), 11.9 (1H, brs).

Step 3: Production of tert-butyl 4-{4-[(1H-benzo[d][1,2,3]triazo-1-yl)oxy]thieno[3,2-d]pyrimidin-7-yl}piperidine-1-carboxylate tert-Butyl 4-(4-oxo-3,4-dihydrothieno[3,2-d]pyrimidin-7-yl)piperidine-1-carboxylate (10.8 mg, 0.032 mmol) and 1H-benzotriazol-1-yloxytripyrrolidinophosphonium hexafluorophosphate (18.4 mg, 0.035 mmol) were dissolved in tetrahydrofuran (1 mL), and then a solution of 1,8-diazabicyclo[5,4,0]-7-undecene (5.7 μL, 0.038 mmol) in dichloromethane (0.5 mL) was added, followed by stirring at room temperature for 20 minutes. The reaction liquid was diluted with water, and then extracted with ethyl acetate. The organic layer was washed with saturated brine, dried over anhydrous sodium sulfate and concentrated under a reduced pressure. The obtained residue was purified by using silica gel chromatography (chloroform:methanol=10:1) to give tert-butyl 4-{4-[(1H-benzo[d][1,2,3]triazo-1-yl)oxy]thieno[3,2-d]pyrimidin-7-yl}piperidine-1-carboxylate (12.3 mg, 84.9%) as a colorless oily substance.
$^1$H-NMR (CDCl$_3$) δ: 1.49 (9H, s), 1.65-1.76 (2H, m), 2.12 (2H, d, J=12.6 Hz), 2.86-3.02 (2H, m), 3.38 (1H, tt, J=3.4, 12.2 Hz), 4.29 (2H, brs), 7.46-7.52 (2H, m), 7.54-7.59 (1H, m), 7.72 (1H, s), 8.13-8.18 (1H, m), 8.66 (1H, s).

Step 4: Production of tert-butyl 4-(4-{[2-fluoro-4-(methylsulfonyl)phenyl]amino}thieno[3,2-d]pyrimidin-7-yl)piperidin-1-carboxylate tert-Butyl 4-{4-[(1H-benzo[d][1,2,3]triazo-1-yl)oxy]thieno[3,2-d]pyrimidin-7-yl}piperidine-1-carboxylate (10.8 mg, 0.032 mmol) and 2-fluoro-4-methylsulfonylaniline (4.1 mg, 0.022 mmol) were dissolved in N,N-dimethylformamide (1 mL), sodium hydride (50% in oil, 2.3 mg, 0.054 mmol) was added, followed by stirring at 70° C. for 1 hour. The reaction liquid was diluted with water and extracted with ethyl acetate. The organic layer was washed with saturated brine, dried over anhydrous sodium sulfate and concentrated under a reduced pressure. The obtained residue was purified by using silica gel chromatography (hexane:acetone=2:1) to give the titled compound (6.7 mg, 49.0%) as a pale yellow amorphous.

Example 28

Production of tert-butyl 4-(4-{[2-fluoro-4-(methylsulfonyl)phenyl]amino}-5H-pyrrolo[3,2-d]pyrimidin-7-yl)piperidine-1-carboxylate Step 1: Production of tert-butyl 4-[4-amino-5-(ethoxycarbonyl)-1H-pyrrol-3-yl]piperidine-1-carboxylate The tert-butyl 4-(1-cyano-2-oxoethyl)piperidine-1-carboxylate (757 mg, 3.0 mmol) obtained in Step 4 of Example 1 was dissolved in methanol (6 mL) and water (2 mL), diethyl aminomalonate hydrochloride (952 mg, 4.5 mmol) and sodium acetate (492 mg, 6.0 mmol) were added, followed by stirring at room temperature for 18 hours. The reaction liquid was concentrated under a reduced pressure and dissolved in chloroform. The organic layer was washed with saturated brine, dried over anhydrous sodium sulfate and concentrated under a reduced pressure. The obtained residue (1.53 g) was dissolved in ethanol (6 mL), and then sodium ethoxide (510 mg, 7.5 mmol) was added, followed by heating under reflux for 3 hours. The reaction liquid was concentrated under a reduced pressure, and the obtained residue was dissolved in ethyl acetate. The organic layer was washed with saturated brine, dried over anhydrous sodium sulfate and concentrated under a reduced pressure. The obtained residue was purified by using silica gel chromatography (chloroform:methanol=100:1→50:1) to give tert-butyl 4-[4-amino-5-(ethoxycarbonyl)-1H-pyrrol-3-yl]piperidine-1-carboxylate (466 mg, 46.0%) as a pale yellow amorphous.

$^1$H-NMR (CDCl$_3$) δ: 1.35 (3H, t, J=7.1 Hz), 1.47 (9H, s), 1.88 (2H, d, J=13.1 Hz), 2.41-2.53 (1H, m), 2.74-2.87 (2H, m), 4.06-4.41 (6H, m), 6.51 (1H, brs), 8.08 (1H, brs).

Step 2: Production of tert-butyl 4-(4-oxo-4,5-dihydro-3H-pyrrolo[3,2-d]pyrimidin-7-yl)piperidine-1-carboxylate tert-Butyl 4-[4-amino-5-(ethoxycarbonyl)-1H-pyrrol-3-yl]piperidine-1-carboxylate (466 mg, 1.38 mmol) was dissolved in ethanol (8 mL), and then formamidine acetate (863 mg, 8.29 mmol) was added, followed by heating under reflux for 14 hours. The reaction liquid was cooled, and the precipitated solid was filtered and washed with ethanol to give tert-butyl 4-(4-oxo-4,5-dihydro-3H-pyrrolo[3,2-d]pyrimidin-7-yl)piperidine-1-carboxylate (452 mg, >1000) as a pale yellow solid.

$^1$H-NMR (d$_6$-DMSO) δ: 1.41 (9H, s), 1.50-1.63 (2H, m), 1.89 (2H, d, J=12.2 z), 2.70-2.92 (1H, m), 3.26-3.39 (2H, m), 3.95-4.08 (2H, m), 7.18 (1H, s), 7.75 (1H, s), 11.7 (1H, brs).

Step 3: Production of tert-butyl 4-(4-chloro-5H-pyrrolo[3,2-d]pyrimidin-7-yl)piperidine-1-carboxylate tert-Butyl 4-(4-oxo-4,5-dihydro-3H-pyrrolo[3,2-d]pyrimidin-7-yl)piperidine-1-carboxylate (466 mg, 1.38 mmol) was dissolved in phosphorus oxychloride (2 mL) and stirred at 100° C. for 5 hours. The reaction liquid was concentrated under a reduced pressure, a 2 N aqueous sodium hydroxide solution (pH=14) was added, and then di-tert-butyl dicarbonate (602 mg, 2.76 mmol) was added to the aqueous solution, followed by stirring at room temperature for 2 hours. The reaction liquid was diluted with water, and extracted with ethyl acetate. The organic layer was washed with saturated brine, dried over anhydrous sodium sulfate and concentrated under a reduced pressure. The obtained residue was purified by using silica gel chromatography (chloroform:methanol=10:1) to give tert-butyl 4-(4-chloro-5H-pyrrolo[3,2-d]pyrimidin-7-yl)piperidine-1-carboxylate (201 mg, 43.1%) as a pale yellow amorphous.

$^1$H-NMR (CDCl$_3$) δ: 1.48 (9H, s), 1.63-1.74 (2H, m), 2.12 2H, d, J=13.1 Hz), 2.82-2.99 (2H, m), 3.18 (1H, tt, J=3.5, 12.1 Hz), 4.23 (2H, brs), 7.40 (1H, s), 8.76 (1H, s), 9.32 (1H, brs).

Step 4: Production of tert-butyl 4-(4-{[2-fluoro-4-(methylsulfonyl)phenyl]amino}-5H-pyrrolo[3,2-d]pyrimidin-7-yl)piperidine-1-carboxylic acid tert-Butyl 4-(4-chloro-5H-pyrrolo[3,2-d]pyrimidin-7-yl)piperidine-1-carboxylate (54.8 mg, 0.163 mmol) was dissolved in 1,4-dioxane (0.5 mL), 2-fluoro-4-methylsulfonylaniline (32.0 mg, 0.169 mmol), tert-butoxysodium (15.9 mg, 0.109 mmol) and bis(tri-tert-butyl-phosphine)palladium (0) (5.8 mg, 0.011 mmol) were added, and the mixture was irradiated with microwave in a sealed tube at 130° C. for 3 hours. The reaction liquid was filtered, the filtrate was concentrated under a reduced pressure, and the obtained residue was purified by using silica gel chromatography (ethyl acetate:hexane=3:1) to give the titled compound (3.6 mg, 6.5%) as a white amorphous.

Example 29

Production of tert-butyl 4-(4-{[2-fluoro-4-(methylsulfonyl)phenyl]amino}-5-(methanesulfonyl)-5H-pyrrolo[3,2-d]pyrimidin-7-yl)piperidine-1-carboxylate tert-Butyl 4-(4-{[2-fluoro-4-(methylsulfonyl)phenyl]amino}-5H-pyrrolo[3,2-d]pyrimidin-7-yl)piperidine-1-carboxylate (3.1 mg, 0.0063 mmol) was dissolved in N,N-dimethylformamide (0.5 mL), sodium hydride (55% in oil, 0.4 mg, 0.0095 mmol) and methanesulfonyl chloride (0.4 mL, 0.0057 mmol) were added under ice-cooling, followed by stirring at room temperature for 3 hours. The reaction liquid was diluted with water, followed by extraction with ethyl acetate. The organic layer was washed with saturated brine, dried over anhydrous sodium sulfate and concentrated under a reduced pressure. The obtained residue was purified by using silica gel chromatography (chloroform:methanol=10:1) to give the titled compound (0.6 mg, 16.8%) as a pale yellow amorphous.

Example 30

Production of tert-butyl 4-(4-{[2-fluoro-4-(methylsulfonyl)phenyl]amino}-5-methyl-5H-pyrrolo[3,2-d]pyrimidin-7-yl)piperidine-1-carboxylate Step 1: Production of tert-butyl 4-(4-chloro-5-methyl-5H-pyrrolo[3,2-d]pyrimidin-7-yl)piperidine-1-carboxylate tert-Butyl 4-(4-chloro-5-methyl-5H-pyrrolo[3,2-d]pyrimidin-7-yl)piperidine-1-carboxylate was obtained as a pale yellow amorphous by reacting and treating in the same manner as in Example 29 by using tert-butyl 4-(4-oxo-4,5-dihydro-3H-pyrrolo[3,2-d]pyrimidin-7-yl)piperidine-1-carboxylate instead of tert-butyl 4-(4-{[2-fluoro-4-(methylsulfonyl)phenyl]amino}-5H-pyrrolo[3,2-d]pyrimidin-7-yl)piperidine-1-carboxylate, and using methyl iodide instead of methanesulfonyl chloride.

$^1$H-NMR (CDCl$_3$) δ: 1.48 (9H, s), 1.56-1.72 (2H, m), 2.07 (2H, d, J=13.1 Hz), 2.86-2.99 (2H, m), 3.15 (1H, tt, J=3.5, 12.0 Hz), 4.11 (3H, s), 4.14-4.30 (2H, brs), 7.15 (1H, s), 8.66 (1H, s).

Step 2: Production of tert-butyl 4-(4-{[2-fluoro-4-(methylsulfonyl)phenyl]amino}-5-methyl-5H-pyrrolo[3,2-d]pyrimidin-7-yl)piperidine-1-carboxylate The titled compound was obtained as a pale yellow amorphous by reacting and treating in the same manner as in Step 4 of Example 28 by using tert-butyl 4-(4-chloro-5-methyl-5H-pyrrolo[3,2-d]pyrimidin-7-yl)piperidine-1-carboxylate instead of tert-butyl 4-(4-chloro-5H-pyrrolo[3,2-d]pyrimidin-7-yl)piperidine-1-carboxylate.

Example 31

Production of N-[2-fluoro-4-(methylsulfonyl)phenyl]-7-{1-[5-(trifluoromethyl)pyrimidin-2-yl]piperidin-4-yl}furo[3,2-d]pyrimidine-4-amine The titled compound was obtained as a white solid by reacting and treating in the same manner as in Step 2 of Example 2 by using 2-(methylsulfinyl)-5-(trifluoromethyl)pyrimidine instead of 2,5-dichloropyrimidine.

Example 32

Production of 2,2,2-trifluoroethyl 4-(4-{[2-fluoro-4-(methylsulfonyl)phenyl]amino}furo[3,2-d]pyrimidin-7-yl)piperidine-1-carboxylate The titled compound was obtained as a white amorphous by reacting and treating in the same manner as in Example 7 by using 2,2,2-trifluoroethyl 1H-imidazole-1-carboxylate instead of benzyl chloroformate.

Example 33

Production of 1,1,1-trifluoro-2-methylpropan-2-yl 4-(4-{[2-fluoro-4-(methylsulfonyl)phenyl]amino}furo[3,2-d]pyrimidin-7-yl)piperidine-1-carboxylate The titled compound was obtained as a white solid by reacting and treating in the same manner as in Example 7 by using 1,1,1-trifluoro-2-methylpropan-2-yl 1H-imidazole-1-carboxylate instead of benzyl chloroformate.

Example 34

Production of 4,4-difluorocyclohexyl 4-(4-{[2-fluoro-4-(methylsulfonyl)phenyl]amino}furo[3,2-d]pyrimidin-7-yl)piperidine-1-carboxylate The titled compound was obtained as a yellow amorphous by reacting and treating in the same manner as in Example 7 by using 4,4-difluorocyclohexyl 1H-imidazole-1-carboxylate instead of benzyl chloroformate.

Example 35

Production of neopentyl 4-(4-{[2-fluoro-4-(methylsulfonyl)phenyl]amino}furo[3,2-d]pyrimidin-7-yl)piperidine-1-carboxylate The titled compound was obtained as a pale yellow amorphous by reacting and treating in the same manner as in Example 7 by using neopentyl chloroformate instead of benzyl chloroformate.

Example 36

Production of 2,2,2-trichloroethyl 4-(4-{[2-fluoro-4-(methylsulfonyl)phenyl]amino}furo[3,2-d]pyrimidin-7-yl)piperidine-1-carboxylate The titled compound was obtained as a white amorphous by reacting and treating in similar manners to those in Example 7 by using 2,2,2-trichloroethyl chloroformate instead of benzyl chloroformate.

Example 37

Production of phenyl 4-(4-{[2-fluoro-4-(methylsulfonyl)phenyl]amino}furo[3,2-d]pyrimidin-7-yl)piperidine-1-carboxylate The titled compound was obtained as a pale yellow amorphous by reacting and treating in the same manner as in Example 7 by using phenyl chloroformate instead of benzyl chloroformate.

Example 38

Production of 1-[4-(4-{[2-fluoro-4-(methylsulfonyl)phenyl]amino}furo[3,2-d]pyrimidin-7-yl)piperidin-1-yl]-3,3-dimethylbutan-1-one The titled compound was obtained as a yellow solid by reacting and treating in the same manner as in Example 7 by using 3,3-dimethylbutanoyl chloride instead of benzyl chloroformate.

Example 39

Production of tert-butyl 4-(4-{[2-fluoro-4-(methylsulfonyl)phenyl](methyl)amino}furo[3,2-d]pyrimidin-7-yl)piperidine-1-carboxylate The titled compound was obtained as a yellow oily substance by reacting and treating in the same manner as in Step 8 of Example 1 by using 2-fluoro-N-methyl-4-(methylsulfonyl)aniline instead of 2-fluoro-4-(methylsulfonyl)aniline.

Example 40

Production of tert-butyl 4-(4-{4-(methylsulfonyl)phenoxy}furo[3,2-d]pyrimidin-7-yl)piperidine-1-carboxylate Under an argon atmosphere, the tert-butyl 4-{4-[(1H-benzo[d][1,2,3]triazol-1-yl)oxy]furo[3,2-d]pyrimidin-7-yl}piperidine-1-carboxylate (10 mg, 0.023 mmol) obtained in Step 7 of Example 1 and 4-(methylsulfonyl)phenol (4 mg, 0.023 mmol) were dissolved in anhydrous N,N-dimethyl formaldehyde (0.5 mL), potassium carbonate (5 mg, 0.035 mmol) was added, stirring was conducted at room temperature for 2 hours, water was added, followed by extraction with toluene. The organic layer was dried over anhydrous sodium sulfate and concentrated under a reduced pressure, and the obtained residue was purified by silica gel preparative thin layer chromatography (hexane:ethyl acetate=1:2) to give the titled compound (10 mg, 89%) as a pale yellow solid.

Example 41

Production of tert-butyl 4-{4-[4-(1H-tetrazol-1-yl)phenoxy]furo[3,2-d]pyrimidin-7-yl}piperidine-1-carboxylate Potassium carbonate (5.0 mg, 0.035 mmol) was added to a solution of the tert-butyl 4-{4-[(1H-benzo[d][1,2,3]triazol-1-yl)oxy]furo[3,2-d]pyrimidin-7-yl}piperidine-1-carboxylate obtained in Step 7 of Example 1 (10.0 mg, 0.023 mmol) and 4-(1H-tetrazol-1-yl)phenol (4.0 mg, 0.025 mmol) in DMF (0.2 mL), followed by stirring at 70° C. for 5 hours. Water was added to the reaction liquid, and the reaction liquid was extracted with chloroform:methanol=5:1 and concentrated under a reduced pressure. The obtained residue was purified by using silica gel chromatography (chloroform:methanol=50:1) to give the titled compound (7.4 mg, 70%) as a white solid.

The compounds obtained by the above-mentioned Examples are shown in Table 1 to Table 9.

TABLE 1

| Example | Structural formula | Physical property value |
|---|---|---|
| 1 | 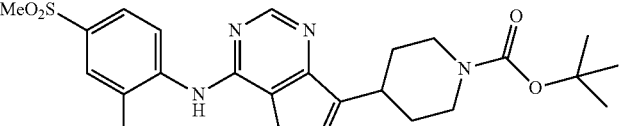 | ¹H-NMR (CDCl₃) δ: 1.48 (9H, s), 1.63-1.75 (2H, m), 2.11-2.19 (2H, m), 2.87-2.97 (2H, m), 3.01-3.13 (1H, m), 3.08 (3H, s), 4.06-4.36 (2H, m), 7.42 (1H, s), 7.64 (1H, s), 7.76 (1H, d, J = 10.2 Hz), 7.81 (1H, dd, J = 1.0, 8.8 Hz), 8.74 (1H, s), 9.07 (1H, t, J = 8.0 Hz). |
| 2 | 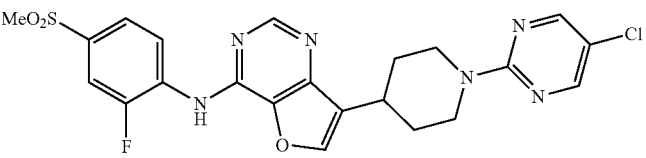 [SMILES: CS(=O)(=O)c1ccc(Nc2ncnc3c(C4CCN(c5ncc(Cl)cn5)CC4)coc23)c(F)c1] | ¹H-NMR (CDCl₃) δ: 1.75 (2H, ddd, J = 3.5, 12.6, 24.8 Hz), 2.22-2.32 (2H, m), 3.04-3.15 (2H, m), 3.08 (3H, s), 3.16-3.25 (1H, m), 4.82-4.90 (2H, m), 7.41 (1H, brs), 7.64 (1H, s), 7.76 (1H, d, J = 9.8 Hz), 7.81 (1H, d, J = 8.8 Hz), 8.23 (2H, s), 8.75 (1H, s), 9.07 (1H, t, J = 8.0 Hz). |
| 3 | 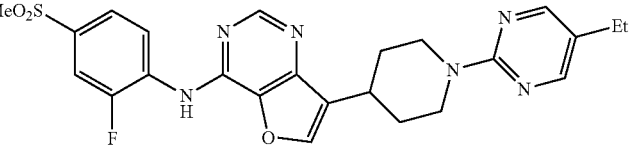 | ¹H-NMR (CDCl₃) δ: 1.20 (3H, t, J = 7.6 Hz), 1.75 (2H, ddd, J = 3.7, 12.4, 25.2 Hz), 2.23-2.30 (2H, m), 2.48 (2H, q, J = 7.6 Hz), 3.03-3.12 (2H, m), 3.08 (3H, s), 3.19 (1H, dddd, J = 3.2, 3.4, 11.8, 12.0 Hz), 4.82-4.92 (2H, m), 7.41 (1H, br s), 7.64 (1H, s), 7.75 (1H, dd, J = 10.2, 2.0 Hz), 7.79-7.84 (1H, m), 8.19 (2H, s), 8.76 (1H, s), 9.08 (1H, t, J = 8.3 Hz). |
| 4 | 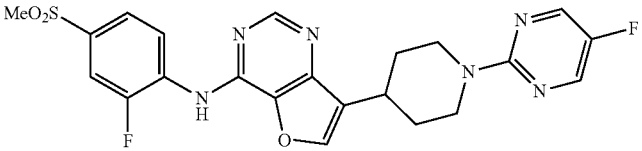 [SMILES: CS(=O)(=O)c1ccc(Nc2ncnc3c(C4CCN(c5ncc(F)cn5)CC4)coc23)c(F)c1] | ¹H-NMR (CDCl₃) δ: 1.76 (2H, ddd, J = 3.9, 12.7, 24.9 Hz), 2.21-2.30 (2H, m), 3.03-3.13 (2H, m), 3.08 (3H, s), 3.19 (1H, dddd J = 3.2, 3.4, 11.6, 11.6 Hz), 4.79-4.87 (1H, m), 4.82 (2H, d, J = 13.7 Hz), 7.42 (1H, br s), 7.64 (1H, d, J = 1.0 Hz), 7.75 (1H, dd, J = 2.0, 10.2 Hz), 7.81 (1H, dd, J = 1.5, 8.3 Hz), 8.21 (2H, s), 8.75 (1H, s), 9.07 (1H, t, J = 8.3 Hz). |
| 5 | 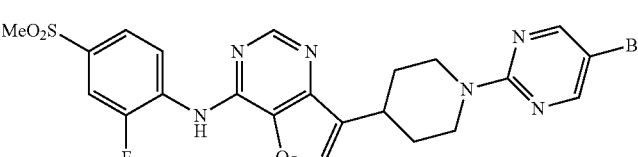 | ¹H-NMR (CDCl₃) δ: 1.75 (2H, ddd, J = 4.0, 12.3, 25.0 Hz), 2.20-2.30 (2H, m), 3.03-3.13 (2H, m), 3.08 (3H, s), 3.20 (1H, dddd, J = 3.6, 3.6, 12.0, 12.0 Hz), 4.80-4.90 (2H, m), 7.42 (1H, br s), 7.64 (1H, s), 7.75 (1H, dd, J = 2.0, 10.2 Hz), 7.79-7.83 (1H, m), 8.30 (2H, s), 8.75 (1H, s), 9.07 (1H, t, J = 8.3 Hz). |

TABLE 2

| Example | Structural formula | Physical property value |
|---|---|---|
| 6 | 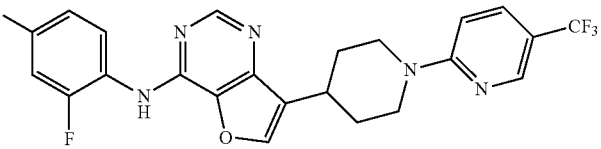 | ¹H-NMR (CDCl₃) δ: 1.80 (2H, ddd, J = 3.9, 12.7, 25.1 Hz), 2.25-2.33 (2H, m), 3.04-3.26 (3H, m), 3.08 (3H, s), 4.53-4.60 (2H, m), 6.70 (1H, d, J = 8.8 Hz), 7.42 (1H, brs), 7.62-7.65 (2H, m), 7.76 (1H, dd, J = 2.0, 10.2 Hz), 7.79-7.83 (1H, m), 8.40-8.42 (1H, m), 8.76 (1H, s), 9.08 (1H, t, J = 8.0 Hz). |
| 7 | 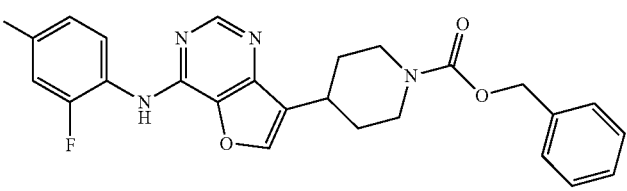 | ¹H-NMR (CDCl₃) δ: 1.65-1.79 (2H, m), 2.12-2.21 (2H, m), 2.95-3.13 (3H, m), 3.08 (3H, s), 4.25-4.42 (2H, m), 5.16 (2H, s), 7.29-7.45 (6H, m), 7.63 (1H, s), 7.75 (1H, dd, J = 2.0, 10.2 Hz), 7.80 (1H, d, J = 8.8 Hz), 8.74 (1H, s), 9.07 (1H, t, J = 8.0 Hz). |

TABLE 2-continued

| Example | Structural formula | Physical property value |
|---|---|---|
| 8 | 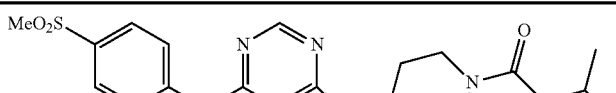 | ¹H-NMR (CDCl₃) δ: 1.26 (6H, d, J = 6.3 Hz), 1.63-1.78 (2H, m), 2.12-2.20 (2H, m), 2.90-3.01 (2H, m), 3.04-3.12 (1H, m), 3.08 (3H, s), 4.28-4.30 (2H, m), 4.94 (1H, quint, J = 6.3 Hz), 7.41 (1H, br s), 7.64 (1H, d, J = 1.0 Hz), 7.75 (1H, dd, J = 2.0, 10.2 Hz), 7.79-7.83 (1H, m), 8.74 (1H, s), 9.07 (1H, t, J = 8.3 Hz). |
| 9 | | ¹H-NMR (CDCl₃) δ: 1.28 (3H, t, J = 7.3 Hz), 1.71 (2H, ddd, J = 3.7, 12.2, 24.6 Hz), 2.12-2.21 (2H, m), 2.90-3.01 (2H, m), 3.04-3.13 (1H, m), 3.08 (3H, s), 4.16 (2H, q, J = 7.2 Hz), 4.24-4.37 (2H, m), 7.42 (1H, br s), 7.64 (1H, s), 7.75 (1H, dd, J = 2.0, 10.2 Hz), 7.79-7.83 (1H, m), 8.74 (1H, s), 9.07 (1H, t, J = 8.3 Hz). |

TABLE 3

| Example | Structural formula | Physical property value |
|---|---|---|
| 10 | | ¹H-NMR (CDCl₃) δ: 1.65-1.79 (2H, m), 2.12-2.21 (2H, m), 2.95-3.13 (3H, m), 3.08 (3H, s), 4.25-4.42 (2H, m), 5.16 (2H, s), 7.29-7.45 (6H, m), 7.63 (1H, s), 7.75 (1H, dd, J = 2.0, 10.2 Hz), 7.80 (1H, d, J = 8.8 Hz), 8.74 (1H, s), 9.07 (1H, t, J = 8.0 Hz). |
| 11 | | ¹H-NMR (CDCl₃) δ: 1.00-1.05 (2H, m), 1.18-1.24 (2H, m), 1.89 (2H, ddd, J = 3.8, 12.3, 25.2 Hz), 2.24-2.37 (3H, m), 2.98-3.13 (3H, m), 3.08 (3H, s), 3.91-4.03 (2H, m), 7.43 (1H, brs), 7.66 (1H, d, J = 1.0 Hz), 7.76 (1H, dd, J = 2.0, 10.2 Hz), 7.79-7.83 (1H, m), 8.74 (1H, s), 9.06 (1H, t, J = 8.3 Hz). |
| 12 | | ¹H-NMR (CDCl₃) δ: 1.18-1.96 (6H, m), 2.11-2.28 (3H, m), 2.88-2.98 (1H, m), 3.01-3.14 (2H, m), 3.08 (3H, s), 3.92-4.00 (2H, m), 7.41 (1H, s), 7.65 (1H, s), 7.76 (1H, dd, J = 2.0, 10.2 Hz), 7.81 (1H, d, J = 8.8 Hz), 8.74 (1H, s), 9.07 (1H, t, J = 8.3 Hz). |
| 13 | | ¹H-NMR (DMSO-D₆) δ: 1.86 (2H, ddd, J = 3.5, 12.3, 24.8 Hz), 2.11-2.21 (2H, m), 2.79-2.88 (1H, m), 3.28 (3H, s), 3.70-3.78 (2H, m), 7.31 (1H, dd, J = 3.7, 5.1 Hz), 7.67 (1H, dd, J = 1.2, 3.7 Hz), 7.77 (1H, dd, J = 2.0, 8.3 Hz), 7.86 (1H, dd, J = 2.0, 10.2 Hz), 7.98 (1H, t, J = 8.0 Hz), 8.07 (1H, dd, J = 1.5, 4.9 Hz), 8.20 (1H, s), 8.47 (1H, s), 10.09 (1H, s) |

TABLE 4

| Example | Structural formula | Physical property value |
|---|---|---|
| 14 |  | ¹H-NMR (CDCl₃) δ: 1.88 (2H, ddd, J = 3.7, 12.4, 24.9 Hz), 2.18-2.28 (2H, m), 2.40-2.51 (2H, m), 2.83 (1H, dddd, J = 3.8, 4.0, 12.0, 12.4 Hz), 3.08 (3H, s), 3.88-3.95 (2H, m), 3.90 (3H, s), 7.01 (2H, s), 7.03 (2H, s), 7.41 (1H, br s), 7.62 (1H, s), 7.70-7.77 (3H, m), 7.78-7.83 (1H, m), 8.69 (1H, s), 9.05 (1H, t, J = 8.0 Hz). |

TABLE 4-continued

| Example | Structural formula | Physical property value |
|---|---|---|
| 15 | | ¹H-NMR (CDCl₃) δ: 0.98 (3H, t, J = 7.3 Hz), 1.45-1.51 (2H, m), 2.24-2.30 (4H, m), 2.92-3.06 (5H, m), 3.08 (3H, s), 3.93-4.00 (2H, m), 7.42 (1H, br s), 7.66 (1H, s), 7.76 (1H, dd, J = 1.5, 10.2 Hz), 7.79-7.84 (1H, m), 8.74 (1H, s), 9.07 (1H, t, J = 8.3 Hz). |
| 16 | | ¹H-NMR (CDCl₃) δ: 1.97-2.10 (2H, m), 2.19-2.28 (2H, m), 2.95-3.15 (3H, m), 3.08 (3H, s), 3.53-3.61 (2H, m), 7.40 (1H, br s), 7.64 (1H, s), 7.75 (1H, dd, J = 2.0, 10.2 Hz), 7.78-7.83 (1H, m), 8.74 (1H, s), 9.07 (1H, t, J = 8.3 Hz). |
| 17 | | ¹H-NMR (CDCl₃) δ: 1.37 (9H, s), 1.73 (2H, ddd, J = 3.9, 12.4, 25.1 Hz), 2.15-2.22 (2H, m), 2.90-2.99 (2H, m), 3.01-3.12 (1H, m), 3.08 (3H, s), 3.99-4.08 (2H, m), 4.36 (1H, br s), 7.42 (1H, brs), 7.64 (1H, s), 7.75 (1H, dd, J = 2.0, 10.2 Hz), 7.79-7.84 (1H, m), 8.74 (1H, s), 9.07 (1H, t, J = 8.0 Hz). |
| 18 | | ¹H-NMR (CDCl₃) δ: 1.58 (9H, s), 1.77-1.87 (2H, m), 2.21-2.28 (2H, m), 3.05-3.24 (3H, m), 3.08 (3H, s), 4.74 (2H, br s), 5.44 (1H, s), 7.42 (1H, br s), 7.65 (1H, s), 7.76 (1H, dd, J = 2.0, 10.2 Hz), 7.79-7.83 (1H, m), 8.74 (1H, s), 9.07 (1H, t, J = 8.3 Hz). |

TABLE 5

| Example | Structural formula | Physical property value |
|---|---|---|
| 19 | | ¹H-NMR (CDCl₃) δ: 1.79-1.94 (2H, m), 2.14-2.22 (1H, m), 2.27-2.35 (1H, m), 2.97-3.10 (1H, m), 3.08 (3H, s), 3.17-3.34 (2H, m), 4.04-4.13 (1H, m), 4.86-4.94 (1H, m), 7.33-7.38 (1H, m), 7.44 (1H, s), 7.62-7.69 (2H, m), 7.75 (1H, dd, J = 2.0, 10.2 Hz), 7.79-7.84 (2H, m), 8.60 (1H, d, J = 4.9 Hz), 8.74 (1H, s), 9.07 (1H, t, J = 8.3 Hz). |
| 20 | | ¹H-NMR (CDCl₃) δ: 1.69-1.97 (2H, m), 2.07-2.38 (2H, m), 3.02-3.11 (1H, m), 3.09 (3H, s), 3.17-3.33 (2H, m), 3.81-3.92 (1H, br m), 4.83-4.93 (1H, brm), 7.39 (1H, dd, J = 5.1, 7.6 Hz), 7.43 (1H, s), 7.67 (1H, s), 7.74-7.83 (3H, m), 8.64-8.76 (3H, m), 9.07 (1H, t, J = 8.0 Hz). |
| 21 | | ¹H-NMR (CDCl₃) δ: 1.49 (9H, s), 1.66-1.78 (2H, m), 2.11-2.21 (2H, m), 2.87-2.99 (2H, m), 3.03-3.13 (1H, m), 3.26 (3H, m), 4.19-4.35 (2H, m), 7.22-7.34 (2H, m), 7.74-7.79 (1H, m), 8.06 (1H, t, J = 8.3 Hz), 8.65 (1H, s). |
| 22 | | ¹H-NMR (CDCl₃) δ: 1.48 (9H, s), 1.72 (3H, ddd, J = 4.1, 12.4, 24.9 Hz), 2.11-2.21 (2H, m), 2.47 (3H, s), 2.85-2.98 (2H, m), 3.07 (1H, dddd, J = 3.4, 3.6, 12.0, 12.0 Hz), 4.13-4.37 (2H, m), 7.23-7.29 (1H, m), 7.52 (1H, d, J = 8.3 Hz), 7.72 (1H, s), 8.48 (1H, d, J = 3.9 Hz), 8.57 (1H, s). |

TABLE 5-continued

| Example | Structural formula | Physical property value |
|---|---|---|
| 23 | | $^1$H-NMR (CDCl$_3$) δ: 1.47 (9H, s), 1.56-1.70 (2H, m), 2.09-2.16 (2H, m), 2.85-3.08 (3H, m), 3.04 (3H, s), 4.12-4.33 (2H, m), 4.96 (2H, d, J = 6.3 Hz), 5.53-5.60 (1H, m), 7.49 (1H, d, J = 1.0 Hz), 7.58 (2H, d, J = 8.3 Hz), 7.92 (2H, d, J = 8.3 Hz), 8.51 (1H, s). |

TABLE 6

| Example | Structural formula | Physical property value |
|---|---|---|
| 24 | | $^1$H-NMR (CDCl$_3$) δ: 1.48 (9H, s), 1.53-1.72 (2H, m), 2.11-2.18 (2H, m), 2.85-2.97 (2H, m), 3.01-3.12 (1H, m), 3.06 (3H, s), 3.38 (2H, t, J = 8.8 Hz), 4.15-4.32 (2H, br m), 4.72 (2H, t, J = 8.8 Hz), 7.61 (1H, s), 7.77 (1H, s), 7.83 (1H, d, J = 9.8 Hz), 8.70-8.74 (2H, m). |
| 25 | | $^1$H-NMR (CDCl$_3$) δ: 1.20 (3H, t, J = 7.6 Hz), 1.72 (2H, ddd, J = 4.0, 12.3, 25.0 Hz), 2.23-2.30 (2H, m), 2.47 (2H, q, J = 7.5 Hz), 3.01-3.12 (3H, m), 3.06 (3H, s), 3.15-3.25 (1H, m), 3.38 (2H, t, J = 8.8 Hz), 4.72 (2H, t, J = 8.5 Hz), 4.83-4.91 (2H, m), 7.61 (1H, d, J = 1.0 Hz), 7.76-7.79 (1H, m), 7.83 (1H, dd, J = 8.8, 2.0 Hz), 8.19 (2H, s), 8.70-8.73 (2H, m). |
| 26 | | $^1$H-NMR (CDCl$_3$) δ: 1.73 (2H, ddd, J = 3.9, 12.4, 25.1 Hz), 2.22-2.30 (2H, m), 3.04-3.14 (2H, m), 3.06 (3H, s), 3.21 (1H, dddd, J = 3.4, 3.6, 12.0, 12.0 Hz), 3.38 (2H, t, J = 8.8 Hz), 4.72 (2H, t, J = 8.8 Hz), 4.81-4.89 (2H, m), 7.61 (1H, s), 7.77 (1H, s), 7.83 (1H, dd, J = 9.0, 2.2 Hz), 8.23 (2H, s), 8.69-8.74 (2H, m). |
| 27 | | $^1$H-NMR (CDCl$_3$) δ: 1.49 (9H, s), 1.61-1.70 (2H, m), 2.12 (2H, d, J = 12.9 Hz), 2.86-3.02 (2H, m), 3.09 (3H, s), 3.38 (1H, tt, J = 3.4, 12.1 Hz), 4.27 (2H, brs), 7.02 (1H, brs), 7.51 (1H, s), 7.74-7.84 (2H, m), 8.90 (1H, s), 9.01 (1H, t, J = 8.2 Hz). |
| 28 | | $^1$H-NMR (CDCl$_3$) δ: 1.49 (9H, s), 1.68-1.85 (2H, m), 1.96-2.18 (2H, m), 2.78-2.99 (2H, m), 3.09 (3H, s), 3.11-3.21 (1H, m), 4.05-4.27 (2H, m), 7.11 (1H, s), 7.64 (1H, dd, J = 2.0, 10.2 Hz), 7.73 (1H, d, J = 8.8 Hz), 8.13 (1H, brs), 8.63 (1H, s), 8.92 (1H, t, J = 8.2 Hz), 10.3 (1H, brs). |

TABLE 7

| Example | Structural formula | Physical property value |
|---|---|---|
| 29 | | $^1$H-NMR (CDCl$_3$) δ: 1.49 (9H, s), 1.57-1.69 (2H, m), 2.13 (2H, d, J = 12.7), 2.86-2.99 (2H, m), 3.08 (3H, s), 3.08-3.18 (1H, m), 3.23 (3H, s), 4.25 (2H, brs), 7.50 (1H, s), 7.74 (1H, dd, J = 2.1, 10.1 Hz), 7.79 (1H, d, J = 8.6 Hz), 8.76 (1H, s), 8.98 (1H, t, J = 8.1 Hz), 9.74 (1H, d, J = 3.4 Hz). |

TABLE 7-continued

| Example | Structural formula | Physical property value |
|---|---|---|
| 30 | | $^1$H-NMR (CDCl$_3$) δ: 1.48 (9H, s), 1.56-1.67 (2H, m), 2.09 (2H, d, J = 13.4), 2.81-2.98 (2H, m), 3.07 (3H, s), 3.08-3.19 (1H, m), 4.16 (3H, s), 4.21 (2H, brs), 6.99 (1H, s), 7.73 (1H, dd, J = 2.1, 10.4 Hz), 7.78 (1H, d, J = 8.8 Hz), 8.60 (1H, s), 8.95-9.01 (1H, m). |
| 31 | | $^1$H-NMR (CDCl$_3$) δ: 1.74 (1H, dd, J = 4.1, 12.4 Hz), 1.81 (1H, dd, J = 4.1, 12.4 Hz), 2.26-2.33 (2H, m), 3.08 (3H, s), 3.15 (2H, t, J = 12.0 Hz), 3.22-3.27 (1H, m), 5.05-4.98 (2H, m), 7.42 (1H, s), 7.65 (1H, s), 7.75 (1H, dd, J = 2.0, 10.2 Hz), 7.81 (1H, d, J = 8.8 Hz), 8.49 (2H, s), 8.76 (1H, s), 9.07 (1H, t, J = 8.3 Hz). |
| 32 | | $^1$H-NMR (CDCl$_3$) δ: 1.68-1.86 (2H, m), 2.15-2.26 (2H, m), 2.94-3.16 (6H, m), 4.38-4.21 (2H, m), 4.51 (2H, q, J = 8.6 Hz), 7.41 (1H, s), 7.65 (1H, s), 7.76 (1H, dd, J = 2.0, 10.2 Hz), 7.81 (1H, d, J = 8.8 Hz), 8.74 (1H, s), 9.07 (1H, t, J = 8.3 Hz). |
| 33 | | $^1$H-NMR (CD$_3$OD) δ: 1.67-1.79 (8H, m), 2.08-2.16 (2H, m), 2.93-3.14 (3H, m), 3.17 (3H, s), 4.09-4.26 (2H, m), 7.79 (1H, s), 7.81 (1H, d, J = 2.0 Hz), 7.96 (1H, s), 8.46 (1H, t, J = 8.0 Hz), 8.53 (1H, s). |

TABLE 8

| Example | Structural formula | Physical property value |
|---|---|---|
| 34 | | $^1$H-NMR (CDCl$_3$) δ: 1.52-2.24 (2H, m), 2.91-3.14 (3H, m), 3.09 (3H, s), 4.14-4.42 (2H, m), 4.90 (1H, s), 7.40-7.43 (1H, m), 7.76 (1H, dd, J = 2.0, 10.2 Hz), 7.81 (1H, d, J = 8.3 Hz), 8.75 (1H, s), 9.07 (1H, t, J = 8.3 Hz). |
| 35 | | $^1$H-NMR (CDCl$_3$) δ: 0.96 (9H, s), 1.58-1.78 (2H, m), 2.14-2.23 (2H, m), 2.91-3.15 (3H, m), 3.08 (3H, s), 3.80 (2H, s), 4.40-4.24 (2H, m), 7.42 (1H, s), 7.64 (1H, s), 7.75 (1H, dd, J = 2.0, 10.2 Hz), 7.81 (1H, d, J = 8.8 Hz), 8.75 (1H, s), 9.07 (1H, t, J = 8.0 Hz). |
| 36 | | $^1$H-NMR (CDCl$_3$) δ: 1.75 (1H, dd, J = 3.9, 12.2 Hz), 1.81 (1H, dd, J = 3.9, 12.2 Hz), 2.20-2.27 (2H, m), 2.99-3.18 (3H, m), 3.08 (3H, s), 4.33-4.41 (2H, m), 4.72-4.84 (2H, m), 7.42 (1H, s), 7.65 (1H, d, J = 1.0 Hz), 7.76 (1H, dd, J = 2.0, 10.2 Hz), 7.81 (1H, d, J = 6.8 Hz), 8.74 (1H, s), 9.07 (1H, t, J = 8.0 Hz). |
| 37 | | $^1$H-NMR (CDCl$_3$) δ: 1.82 (1H, dd, J = 4.1, 12.4 Hz), 1.88 (1H, dd, J = 4.1, 12.4 Hz), 2.19-2.31 (2H, m), 3.04-3.26 (3H, m), 3.09 (3H, s), 4.51-4.38 (2H, m), 7.13 (2H, d, J = 7.3 Hz), 7.18-7.23 (1H, m), 7.37 (2H, t, J = 7.3 Hz), 7.44 (1H, s), 7.68 (1H, s), 7.76 (1H, dd, J = 2.0, 10.2 Hz), 7.81 (1H, d, J = 8.8 Hz), 8.76 (1H, s), 9.08 (1H, t, J = 8.3 Hz). |

TABLE 9

| Example | Structural formula | Physical property value |
|---|---|---|
| 38 | (structure) | $^1$H-NMR (CDCl$_3$) δ:<br>1.08 (9H, s), 1.65-1.76 (2H, m), 2.15-2.40 (5H, m), 2.73 (1H, t, J = 12.0 Hz), 3.08 (3H, s), 3.10-3.19 (2H, m), 3.24 (1H, t, J = 12.0 Hz), 4.04-4.12 (1H, m), 4.80-4.89 (1H, m), 7.43 (1H, s), 7.64 (1H, d, J = 1.0 Hz), 7.76 (1H, dd, J = 2.0, 10.2 Hz), 7.81 (1H, d, J = 8.8 Hz), 8.74 (1H, s), 8.74 (1H, s), 9.06 (1H, t, J = 8.0 Hz). |
| 39 | (structure) | $^1$H-NMR (CDCl$_3$) δ:<br>1.47 (9H, s), 1.57-1.65 (2H, m), 2.04-2.14 (2H, m), 2.82-3.05 (3H, m), 3.14 (3H, s), 3.71 (3H, s), 4.12-4.27 (2H, m), 7.36 (1H, s), 7.54 (1H, t, J = 7.8 Hz), 7.76-7.82 (2H, m), 8.59 (1H, s). |
| 40 | (structure) | $^1$H-NMR (CDCl$_3$) δ:<br>1.48 (9H, s), 1.67-1.78 (2H, m), 2.11-2.19 (2H, m), 2.85-2.98 (2H, m), 3.01-3.09 (1H, m), 3.11 (3H, s), 4.19-4.31 (2H, m), 7.50 (2H, dd, J = 2.0, 6.8 Hz), 7.74 (1H, s), 8.06 (2H, d, J = 8.3 Hz), 8.63 (1H, s). |
| 41 | (structure) | $^1$H-NMR (CDCl$_3$) δ:<br>1.49 (9H, s), 1.64-1.80 (2H, m), 2.16 (2H, d, J = 13.6 Hz), 2.84-2.98 (2H, m), 3.02-3.12 (1H, m), 4.18-4.34 (2H, m), 7.53 (2H, d, J = 8.8 Hz), 7.74 (1H, s), 7.82 (2H, d, J = 8.4 Hz), 8.62 (1H, s), 9.00 (1H, s). |

Test Example 1

Action of Promoting Insulin Secretion

Hamster pancreatic β cell strain HIT-T15 cells were subcultured by using a Ham's F-12K culture medium containing penicillin (100 unit/mL), streptomycin (100 μg/mL) and 10% fetal bovine serum. The cells were sown on a 24-well cell culture plate, cultured at 37° C. for 48 hours, and washed with a 0.10 albumin KRBH buffer. Subsequently, the cells were allowed to stand in the same buffer at 37° C. for 1 hour. Glucose was added thereto so as to give a final concentration of 2 mM, and the compound of the present invention that had been dissolved in dimethylsulfoxide at a concentration of 1.000-fold of the respective concentrations (from 0.0001 μM to 10 μM at a common ratio of 10) was further added under a condition that the compound was included in an amount of 0.1 volume % in the buffer. After the addition of the compound of the present invention, the cells were allowed to stand at 37° C. for 1 hour, and the concentration of the insulin included in the supernatant was measured by an insulin kit (SCETI Medical Labo K. K.). A hamster insulin standard solution (SHIBAYAGI Co., Ltd.) was used as a standard solution. A control to which only dimethylsulfoxide had been added was used. The results are shown in Table 8 as the 50% effect concentrations (EC$_{50}$ values, 50% effect concentrations)) of the respective subject compounds. The EC$_{50}$ values were calculated by using a statistical analysis program, SAS Pre-Clinical Package Ver 5.0 (SAS institute Japan Co., Tokyo).

TABLE 10

| Example No. | EC$_{50}$ (nM) |
|---|---|
| 1 | 5.3 |
| 2 | 4.0 |
| 3 | 14.3 |
| 4 | 33.1 |
| 5 | 12.4 |
| 6 | 20.5 |
| 7 | 33.7 |
| 8 | 83.5 |
| 11 | 76.9 |
| 12 | 9.1 |
| 21 | 51.9 |
| 24 | 3.6 |
| 25 | 16.4 |
| 27 | 50.7 |
| 31 | 4.5 |
| 33 | 15.1 |
| 35 | 58.4 |
| 36 | 18.7 |
| 37 | 56.2 |
| 40 | 10.7 |
| 41 | 42.9 |

As mentioned above, it is understood that the compounds of the present invention have a strong effect of promoting insulin secretion.

INDUSTRIAL APPLICABILITY

The condensed pyridine or condensed pyrimidine derivative represented by the general formula (1) or a salt thereof, or a solvate of the compound or the salt of the present invention is industrially applicable since it has an excellent action of promoting insulin secretion and thus is useful for the prophylaxis and/or therapy of diabetes mellitus.

The invention claimed is:

1. A compound of formula (1):

(1)

[Structure showing formula (1) with substituents R¹ through R⁹, A, B, D, X, Y]

wherein:
- one of A and B is a nitrogen atom and the other is a nitrogen atom or $CR^{10}$, wherein $R^{10}$ is a hydrogen atom, a halogen atom, a $C_{1-6}$ alkyl group, a $C_{1-6}$ alkoxy group, an amino group, or a nitro group;
- D is a nitrogen atom or $CR^{11}$, wherein $R^{11}$ is a hydrogen atom, a halogen atom, a $C_{1-6}$ alkyl group, a $C_{1-6}$ alkoxy group, an amino group, or a nitro group;
- X is an oxygen atom, a sulfur atom, or —$(CH_2)$n-N$(R^{12})$—, wherein $R^{12}$ is a hydrogen atom or a $C_{1-6}$ alkyl group, and n is 0 or 1;
- Y is an oxygen atom, a sulfur atom, or —$N(R^{13})$—, wherein $R^{13}$ is a hydrogen atom, a $C_{1-6}$ alkyl group, or a substituted sulfonyl group;
- $R^1$, $R^3$, and $R^4$ are each independently a hydrogen atom, a halogen atom, a $C_{1-6}$ alkyl group, a $C_{1-6}$ alkoxy group, an amino group, or a nitro group, or
- $R^1$ and $R^{12}$ together form a nitrogen-comprising heterocycle;
- $R^2$ is a hydrogen atom, —$S(O)R^{14}$, —$S(O)_2R^{15}$, —$CO_2R^{16}$, —$CONR^{17}R^{18}$ wherein $R^{14}$ and $R^{15}$ are each a $C_{1-6}$ alkyl group, a $C_{3-8}$ cycloalkyl group, a $C_{2-6}$ alkenyl group, a $C_{2-6}$ alkynyl group, an amino group, a mono($C_{1-6}$ alkyl)amino group, or a di($C_{1-6}$ alkyl)amino group, $R^{16}$ is a $C_{1-6}$ alkyl group, and $R^{17}$ and $R^{18}$ are each independently a hydrogen atom or a $C_{1-6}$ alkyl group optionally comprising a substituent, or a 5-10 membered heteroaryl group optionally comprising a substituent;
- $R^5$ is a hydrogen atom, a halogen atom, a $C_{1-6}$ alkyl group, a $C_{1-6}$ alkoxy group, a $C_{1-6}$ alkylthio group, or an amino group;
- $R^6$ is a hydrogen atom, a halogen atom, a $C_{1-6}$ alkyl group, or an amino group;
- $R^7$ and $R^8$ are each independently a hydrogen atom or a $C_{1-6}$ alkyl group; and
- $R^9$ is a $C_{1-6}$ alkyl group, —$C(O)R^{19}$, —$C(S)R^{20}$, —$S(O)_2R^{21}$, a $C_{6-10}$ aryl group optionally comprising a substituent or a 5-10 membered heteroaryl group optionally comprising a substituent wherein $R^{19}$ is a $C_{1-6}$ alkyl group, a $C_{1-6}$ alkoxy group, a halo $C_{1-6}$ alkyl group, a halo $C_{1-6}$ alkoxy group, a $C_{3-8}$ cycloalkyl group, a $C_{3-8}$ cycloalkoxy group, a halo $C_{3-8}$ cycloalkyl group, a halo $C_{3-8}$ cycloalkoxy group, a $C_{6-10}$ aryl group, a $C_{6-10}$ aryloxy group, a $C_{6-10}$ aryl $C_{1-6}$ alkoxy group, a 5-10 membered heteroaryl group optionally comprising a substituent, or a mono($C_{1-6}$ alkyl)amino group, $R^{20}$ and $R^{21}$ are a $C_{1-6}$ alkyl group, a halo $C_{1-6}$ alkyl group, a $C_{3-8}$ cycloalkyl group, a mono($C_{1-6}$ alkyl)amino group, a $C_{6-10}$ aryl group optionally comprising a substituent or a 5-10 membered heteroaryl group optionally comprising a substituent, or a salt thereof, or a solvate of the compound or the salt.

2. The compound of claim 1, wherein the nitrogen-comprising heterocycle formed by $R^1$ and $R^{12}$ together has a formula selected from the group consisting of:

[Six heterocyclic structures shown]

and or a salt thereof, or a solvate of the compound or the salt.

3. The compound of claim 1, which is selected from the following compound group, or a salt thereof, or a solvate of the compound or the salt:
- tert-butyl 4-(4-{[2-fluoro-4-(methylsulfonyl)phenyl]amino}furo[3,2-d]pyrimidin-7-yl)piperidine-1-carboxylate;
- 7-[1-(5-chloropyrimidin-2-yl)piperidin-4-yl]-N-[2-fluoro-4-(methylsulfonyl)phenyl]furo[3,2-d]pyrimidine-4-amine;
- 7-[1-(5-ethylpyrimidin-2-yl)piperidin-4-yl]-N-[2-fluoro-4-(methylsulfonyl)phenyl]furo[3,2-d]pyrimidine-4-amine;
- N-[2-fluoro-4-(methylsulfonyl)phenyl]-7-[1-(5-fluoropyrimidin-2-yl)piperidin-4-yl]furo[3,2-d]pyrimidine-4-amine;
- 7-[1-(5-bromopyrimidin-2-yl)piperidin-4-yl]-N-[2-fluoro-4-(methylsulfonyl)phenyl]furo[3,2-d]pyrimidine-4-amine;
- N-[2-fluoro-4-(methylsulfonyl)phenyl]-7-{1-[5-(trifluoromethyl)pyridin-2-yl]piperidin-4-yl}furo[3,2-d]pyrimidine-4-amine;
- benzyl 4-(4-{[2-fluoro-4-(methylsulfonyl)phenyl]amino}furo[3,2-d]pyrimidin-7-yl)piperidine-1-carboxylate;
- isopropyl 4-(4-{[2-fluoro-4-(methylsulfonyl)phenyl]amino}furo[3,2-d]pyrimidin-7-yl)piperidine-1-carboxylate;
- ethyl 4-(4-{[2-fluoro-4-(methylsulfonyl)phenyl]amino}furo[3,2-d]pyrimidin-7-yl)piperidine-1-carboxylate;
- 7-(1-{[3,5-bis(trifluoromethyl)phenyl]sulfonyl}piperidin-4-yl)-N-[2-fluoro-4-(methylsulfonyl)phenyl]furo[3,2-d]pyrimidine-4-amine;
- 7-[1-(cyclopropylsulfonyl)piperidin-4-yl]-N-[2-fluoro-4-(methylsulfonyl)phenyl]furo[3,2-d]pyrimidine-4-amine;
- 7-[1-(cyclohexylsulfonyl)piperidin-4-yl]-N-[2-fluoro-4-(methylsulfonyl)phenyl]furo[3,2-d]pyrimidine-4-amine;
- N-[2-fluoro-4-(methylsulfonyl)phenyl]-7-[1-(thiophen-2-ylsulfonyl)piperidin-4-yl]furo[3,2-d]pyrimidine-4-amine;
- N-[2-fluoro-4-(methylsulfonyl)phenyl]-7-{1-[(4-methoxyphenyl)sulfonyl]piperidin-4-yl}furo[3,2-d]pyrimidine-4-amine;
- 7-[1-(butylsulfonyl)piperidin-4-yl]-N-[2-fluoro-4-(methylsulfonyl)phenyl]furo[3,2-d]pyrimidine-4-amine;
- N-[2-fluoro-4-(methylsulfonyl)phenyl]-7-{1-[(trichloromethyl)sulfonyl]piperidin-4-yl}furo[3,2-d]pyrimidine-4-amine;

N-(tert-butyl)-4-(4-{[2-fluoro-4-(methylsulfonyl)phenyl] amino}furo[3,2-d]pyrimidin-7-yl)piperidine-1-carboxamide;
N-(tert-butyl)-4-(4-{[2-fluoro-4-(methylsulfonyl)phenyl] amino}furo[3,2-d]pyrimidin-7-yl)piperidine-1-carbothioamide;
[4-(4-{[2-fluoro-4-(methylsulfonyl)phenyl]amino}furo [3,2-d]pyrimidin-7-yl) piperidin-1-yl](pyridin-2-yl) methanone;
[4-(4-{[2-fluoro-4-(methylsulfonyl)phenyl]amino}furo [3,2-d]pyrimidin-7-yl) piperidin-1-yl](pyridin-3-yl) methanone;
tert-butyl 4-{4-[3-fluoro-4-(methylsulfonyl)phenoxy]furo [3,2-d]pyrimidin-7-yl}piperidine-1-carboxylate;
tert-butyl 4-{4-[(2-methylpyridin-3-yl)oxy]furo[3,2-d]pyrimidin-7-yl}piperidine-1-carboxylate;
tert-butyl 4-(4-{[4-(methylsulfonyl)benzyl]amino}furo[3,2-d]pyrimidin-7-yl)piperidine-1-carboxylate;
tert-butyl 4-{4-[5-(methylsulfonyl)indolin-1-yl]furo[3,2-d]pyrimidin-7-yl}piperidine-1-carboxylate;
7-[1-(5-ethylpyrimidin-2-yl)piperidin-4-yl]-4-[5-(methylsulfonyl)indolin-1-yl]furo[3,2-d]pyrimidine;
7-[1-(5-chloropyrimidin-2-yl)piperidin-4-yl]-4-[5-(methylsulfonyl)indolin-1-yl]furo[3,2-d]pyrimidine;
tert-butyl 4-(4-{[2-fluoro-4-(methylsulfonyl)phenyl] amino}thieno[3,2-d]pyrimidin-7-yl)piperidine-1-carboxylate;
tert-butyl 4-(4-{[2-fluoro-4-(methylsulfonyl)phenyl] amino}-5H-pyrrolo[3,2-d]pyrimidin-7-yl)piperidine-1-carboxylate;
tert-butyl 4-(4-{[2-fluoro-4-(methylsulfonyl)phenyl] amino}-5-(methanesulfonyl)-5H-pyrrolo[3,2-d]pyrimidin-7-yl)piperidine-1-carboxylate;
tert-butyl 4-(4-{[2-fluoro-4-(methylsulfonyl)phenyl] amino}-5-methyl-5H-pyrrolo[3,2-d]pyrimidin-7-yl)piperidine-1-carboxylate;
N-[2-fluoro-4-(methylsulfonyl)phenyl]-7-{1-[5-(trifluoromethyl)pyrimidin-2-yl]piperidin-4-yl}furo[3,2-d]pyrimidine-4-amine;
2,2,2-trifluoroethyl 4-(4-{[2-fluoro-4-(methylsulfonyl) phenyl]amino}furo[3,2-d]pyrimidin-7-yl)piperidine-1-carboxylate;
1,1,1-trifluoro-2-methylpropan-2-yl 4-(4-{[2-fluoro-4-(methylsulfonyl)phenyl]amino}furo[3,2-d]pyrimidin-7-yl)piperidine-1-carboxylate;
4,4-difluorocyclohexyl 4-(4-{[2-fluoro-4-(methylsulfonyl)phenyl]amino}furo[3,2-d]pyrimidin-7-yl)piperidine-1-carboxylate;
neopentyl 4-(4-{[2-fluoro-4-(methylsulfonyl)phenyl] amino}furo[3,2-d]pyrimidin-7-yl)piperidine-1-carboxylate;
2,2,2-trichloroethyl 4-(4-{[2-fluoro-4-(methylsulfonyl) phenyl]amino}furo[3,2-d]pyrimidin-7-yl)piperidine-1-carboxylate;
phenyl 4-(4-{[2-fluoro-4-(methylsulfonyl)phenyl] amino}furo[3,2-d]pyrimidin-7-yl)piperidine-1-carboxylate;
1-[4-(4-{[2-fluoro-4-(methylsulfonyl)phenyl]amino}furo [3,2-d]pyrimidin-7-yl)piperidin-1-yl]-3,3-dimethylbutan-1-one;
tert-butyl 4-(4-{[2-fluoro-4-(methylsulfonyl)phenyl](methyl)amino}furo[3,2-d]pyrimidin-7-yl)piperidine-1-carboxylate;
tert-butyl 4-(4-{4-(methylsulfonyl)phenoxy}furo[3,2-d] pyrimidin-7-yl)piperidine-1-carboxylate; and
tert-butyl 4-{4-[4-(1H-tetrazol-1-yl)phenoxy]furo[3,2-d] pyrimidin-7-yl}piperidine-1-carboxylate.

4. A compound represented by the following formula (1):

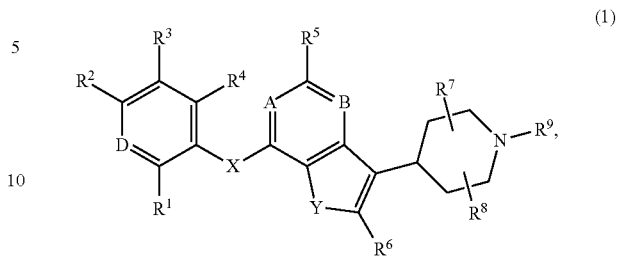

wherein:
one of A and B is a nitrogen atom and the other is a nitrogen atom or $CR^{10}$, wherein $R^{10}$ is a hydrogen atom, a halogen atom, a $C_{1-6}$ alkyl group, a $C_{1-6}$ alkoxy group, an amino group, or a nitro group;
D is a nitrogen atom or $CR^{11}$, wherein $R^{11}$ is a hydrogen atom, a halogen atom, a $C_{1-6}$ alkyl group, a $C_{1-6}$ alkoxy group, an amino group, or a nitro group;
X is an oxygen atom, a sulfur atom, or —(CH$_2$)n-N (R$^{12}$)—, wherein $R^{12}$ is a hydrogen atom or a $C_{1-6}$ alkyl group, and n is 0 or 1;
Y is an oxygen atom, a sulfur atom, or —N(R$^{13}$)—, wherein $R^{13}$ is a hydrogen atom, a $C_{1-6}$ alkyl group, or a substituted sulfonyl group;
$R^1$, $R^3$, and $R^4$ are each independently a hydrogen atom, a halogen atom, a $C_{1-6}$ alkyl group, a $C_{1-6}$ alkoxy group, an amino group, or a nitro group;
$R^2$ is a hydrogen atom, —S(O)R$^{14}$, —S(O)R$^{14}$, —CO$_2$R$^{16}$, —CONR$^{17}$R$^{18}$ wherein $R^{14}$ and $R^{15}$ are each a $C_{1-6}$ alkyl group, a $C_{3-8}$ cycloalkyl group, a $C_{2-6}$ alkenyl group, a $C_{2-6}$ alkynyl group, an amino group, a mono($C_{1-6}$ alkyl) amino group, or a di($C_{1-6}$ alkyl)amino group, $R^{16}$ is a $C_{1-6}$ alkyl group, and $R^{17}$ and $R^{18}$ are each independently a hydrogen atom or a $C_{1-6}$ alkyl group optionally comprising a substituent), or a 5-10 membered heteroaryl group optionally comprising a substituent;
$R^5$ is a hydrogen atom, a halogen atom, a $C_{1-6}$ alkyl group, a $C_{1-6}$ alkoxy group, a $C_{1-6}$ alkylthio group, or an amino group;
$R^6$ is a hydrogen atom, a halogen atom, a $C_{1-6}$ alkyl group, or an amino group;
$R^7$ and $R^8$ are each independently a hydrogen atom or a $C_{1-6}$ alkyl group;
$R^9$ is a $C_{1-6}$ alkyl group, —C(O)R$^{19}$, —C(S)R$^{20}$, —S(O)$_2$R$^{21}$, a $C_{6-10}$ aryl group optionally comprising a substituent or a 5-10 membered heteroaryl group optionally comprising a substituent wherein $R^{19}$ is a $C_{1-6}$ alkyl group, a $C_{1-6}$ alkoxy group, a halo $C_{1-6}$ alkyl group, a halo $C_{1-6}$ alkoxy group, a $C_{3-8}$ cycloalkyl group, a halo $C_{3-8}$ cycloalkyl group, a $C_{3-8}$ cycloalkoxy group, a halo $C_{3-8}$ cycloalkoxy group, a $C_{6-10}$ aryl group, a $C_{6-10}$ aryloxy group, a $C_{6-10}$ aryl $C_{1-6}$ alkoxy group, a 5-10 membered heteroaryl group optionally comprising a substituent or a mono($C_{1-6}$ alkyl)amino group, $R^{20}$ and $R^{21}$ are each a $C_{1-6}$ alkyl group, a halo $C_{1-6}$ alkyl group, a $C_{3-8}$ cycloalkyl group, a mono($C_{1-6}$ alkyl)amino group, a $C_{6-10}$ aryl group optionally comprising a substituent, or a 5-10 membered heteroaryl group optionally comprising a substituent),
or a salt thereof, or a solvate of the compound or the salt.

5. The compound of claim 4, which is selected from the following compound group, or a salt thereof, or a solvate of the compound or the salt:

tert-butyl 4-(4-{[2-fluoro-4-(methylsulfonyl)phenyl]amino}furo[3,2-d]pyrimidin-7-yl)piperidine-1-carboxylate;
7-[1-(5-chloropyrimidin-2-yl)piperidin-4-yl]-N-[2-fluoro-4-(methylsulfonyl)phenyl]furo[3,2-d]pyrimidine-4-amine;
7-[1-(5-ethylpyrimidin-2-yl)piperidin-4-yl]-N-[2-fluoro-4-(methylsulfonyl)phenyl]furo[3,2-d]pyrimidine-4-amine;
N-[2-fluoro-4-(methylsulfonyl)phenyl]-7-[1-(5-fluoropyrimidin-2-yl)piperidin-4-yl]furo[3,2-d]pyrimidine-4-amine;
7-[1-(5-bromopyrimidin-2-yl)piperidin-4-yl]-N-[2-fluoro-4-(methylsulfonyl)phenyl]furo[3,2-d]pyrimidine-4-amine;
N-[2-fluoro-4-(methylsulfonyl)phenyl]-7-{1-[5-(trifluoromethyl)pyridin-2-yl]piperidin-4-yl}furo[3,2-d]pyrimidine-4-amine;
benzyl 4-(4-{[2-fluoro-4-(methylsulfonyl)phenyl]amino}furo[3,2-d]pyrimidin-7-yl)piperidine-1-carboxylate;
isopropyl 4-(4-{[2-fluoro-4-(methylsulfonyl)phenyl]amino}furo[3,2-d]pyrimidin-7-yl)piperidine-1-carboxylate;
ethyl 4-(4-{[2-fluoro-4-(methylsulfonyl)phenyl]amino}furo[3,2-d]pyrimidin-7-yl)piperidine-1-carboxylate;
7-(1-{[3,5-bis(trifluoromethyl)phenyl]sulfonyl}piperidin-4-yl)-N-[2-fluoro-4-(methylsulfonyl)phenyl]furo[3,2-d]pyrimidine-4-amine;
7-[1-(cyclopropylsulfonyl)piperidin-4-yl]-N-[2-fluoro-4-(methylsulfonyl)phenyl]furo[3,2-d]pyrimidine-4-amine;
7-[1-(cyclohexylsulfonyl)piperidin-4-yl]-N-[2-fluoro-4-(methylsulfonyl)phenyl]furo[3,2-d]pyrimidine-4-amine;
N-[2-fluoro-4-(methylsulfonyl)phenyl]-7-[1-(thiophen-2-ylsulfonyl)piperidin-4-yl]furo[3,2-d]pyrimidine-4-amine;
N-[2-fluoro-4-(methylsulfonyl)phenyl]-7-{1-[(4-methoxyphenyl)sulfonyl]piperidin-4-yl}furo[3,2-d]pyrimidine-4-amine;
7-[1-(butylsulfonyl)piperidin-4-yl]-N-[2-fluoro-4-(methylsulfonyl)phenyl]furo[3,2-d]pyrimidine-4-amine;
N-[2-fluoro-4-(methylsulfonyl)phenyl]-7-{1-[(trichloromethyl)sulfonyl]piperidin-4-yl}furo[3,2-d]pyrimidine-4-amine;
N-(tert-butyl)-4-(4-{[2-fluoro-4-(methylsulfonyl)phenyl]amino}furo[3,2-d]pyrimidin-7-yl)piperidine-1-carboxamide;
N-(tert-butyl)-4-(4-{[2-fluoro-4-(methylsulfonyl)phenyl]amino}furo[3,2-d]pyrimidin-7-yl)piperidine-1-carbothioamide;
[4-(4-{[2-fluoro-4-(methylsulfonyl)phenyl]amino}furo[3,2-d]pyrimidin-7-yl)piperidin-1-yl](pyridin-2-yl)methanone;
[4-(4-{[2-fluoro-4-(methylsulfonyl)phenyl]amino}furo[3,2-d]pyrimidin-7-yl)piperidin-1-yl](pyridin-3-yl)methanone;
tert-butyl 4-{4-[3-fluoro-4-(methylsulfonyl)phenoxy]furo[3,2-d]pyrimidin-7-yl}piperidine-1-carboxylate;
tert-butyl 4-{4-[(2-methylpyridin-3-yl)oxy]furo[3,2-d]pyrimidin-7-yl}piperidine-1-carboxylate;
tert-butyl 4-(4-{[4-(methylsulfonyl)benzyl]amino}furo[3,2-d]pyrimidin-7-yl)piperidine-1-carboxylate;
tert-butyl 4-(4-{[2-fluoro-4-(methylsulfonyl)phenyl]amino}thieno[3,2-d]pyrimidin-7-yl)piperidine-1-carboxylate;
tert-butyl 4-(4-{[2-fluoro-4-(methylsulfonyl)phenyl]amino}-5H-pyrrolo[3,2-d]pyrimidin-7-yl)piperidine-1-carboxylate;
tert-butyl 4-(4-{[2-fluoro-4-(methylsulfonyl)phenyl]amino}-5-(methanesulfonyl)-5H-pyrrolo[3,2-d]pyrimidin-7-yl)piperidine-1-carboxylate;
tert-butyl 4-(4-{[2-fluoro-4-(methylsulfonyl)phenyl]amino}-5-methyl-5H-pyrrolo[3,2-d]pyrimidin-7-yl)piperidine-1-carboxylate;
N-[2-fluoro-4-(methylsulfonyl)phenyl]-7-{1-[5-(trifluoromethyl)pyrimidin-2-yl]piperidin-4-yl}furo[3,2-d]pyrimidine-4-amine;
2,2,2-trifluoroethyl 4-(4-{[2-fluoro-4-(methylsulfonyl)phenyl]amino}furo[3,2-d]pyrimidin-7-yl)piperidine-1-carboxylate;
1,1,1-trifluoro-2-methylpropan-2-yl 4-(4-{[2-fluoro-4-(methylsulfonyl)phenyl]amino}furo[3,2-d]pyrimidin-7-yl)piperidine-1-carboxylate;
4,4-difluorocyclohexyl 4-(4-{[2-fluoro-4-(methylsulfonyl)phenyl]amino}furo[3,2-d]pyrimidin-7-yl)piperidine-1-carboxylate;
neopentyl 4-(4-{[2-fluoro-4-(methylsulfonyl)phenyl]amino}furo[3,2-d]pyrimidin-7-yl)piperidine-1-carboxylate;
2,2,2-trichloroethyl 4-(4-{[2-fluoro-4-(methylsulfonyl)phenyl]amino}furo[3,2-d]pyrimidin-7-yl)piperidine-1-carboxylate;
phenyl 4-(4-{[2-fluoro-4-(methylsulfonyl)phenyl]amino}furo[3,2-d]pyrimidin-7-yl)piperidine-1-carboxylate;
1-[4-(4-{[2-fluoro-4-(methylsulfonyl)phenyl]amino}furo[3,2-d]pyrimidin-7-yl)piperidin-1-yl]-3,3-dimethylbutan-1-one;
tert-butyl 4-(4-{[2-fluoro-4-(methylsulfonyl)phenyl](methyl)amino}furo[3,2-d]pyrimidin-7-yl)piperidine-1-carboxylate;
tert-butyl 4-(4-{4-(methylsulfonyl)phenoxy}furo[3,2-d]pyrimidin-7-yl)piperidine-1-carboxylate; and
tert-butyl 4-{4-[4-(1H-tetrazol-1-yl)phenoxy]furo[3,2-d]pyrimidin-7-yl}piperidine-1-carboxylate.

6. A pharmaceutical composition, comprising:
the compound of claim 1 or a salt thereof, or a solvate of the compound or the salt; and
a pharmaceutically acceptable carrier.

7. An insulin secretagogue, comprising:
an active ingredient comprising the compound of claim 1 or a salt thereof, or a solvate of the compound or the salt.

8. A hypoglycemic agent, comprising an active ingredient comprising the compound of claim 1 or a salt thereof, or a solvate of the compound or the salt.

9. A therapeutic agent, comprising:
an active ingredient comprising the compound of claim 1 or a salt thereof, or a solvate of the compound or the salt.

10. A method for promoting insulin secretion, the method comprising:
administering to a patient in need thereof an effective amount of the compound of claim 1 or a salt thereof, or a solvate of the compound or the salt.

11. A method for decreasing blood glucose, the method comprising:
administering to a patient in need thereof an effective amount of the compound of claim 1 or a salt thereof, or a solvate of the compound or the salt.

12. A method for treating diabetes mellitus, the method comprising:
   administering to a patient in need thereof an effective amount of the compound of claim 1 or a salt thereof, or a solvate of the compound or the salt.

13. A pharmaceutical composition, comprising:
   the compound of claim 4 or a salt thereof, or a solvate of the compound or the salt; and
   a pharmaceutically acceptable carrier.

14. An insulin secretagogue, comprising:
   an active ingredient comprising the compound of claim 4 or a salt thereof, or a solvate of the compound or the salt.

15. A hypoglycemic agent, comprising:
   an active ingredient comprising the compound of claim 4 or a salt thereof, or a solvate of the compound or the salt.

16. A therapeutic agent, comprising:
   an active ingredient comprising the compound of claim 4 or a salt thereof, or a solvate of the compound or the salt.

17. A method for promoting insulin secretion, the method comprising:
   administering to a patient in need thereof an effective amount of the compound of claim 4 or a salt thereof, or a solvate of the compound or the salt.

18. A method for decreasing blood glucose, the method comprising:
   administering to a patient in need thereof an effective amount of the compound of claim 4 or a salt thereof, or a solvate of the compound or the salt.

19. A method for treating diabetes mellitus, the method comprising:
   administering to a patient in need thereof an effective amount of the compound of claim 4 or a salt thereof, or a solvate of the compound or the salt.

* * * * *